US007183058B2

(12) United States Patent
Lyons et al.

(10) Patent No.: US 7,183,058 B2
(45) Date of Patent: Feb. 27, 2007

(54) CARRIER TESTS FOR ALBINISM IN THE CAT

(76) Inventors: Leslie A. Lyons, 1355 Tyler Dr., Woodland, CA (US) 95776; Donna L. Imes, 510 Lake Blvd., #151, Davis, CA (US) 95616

(*) Notice: Subject to any disclaimer, the term of this patent is extended or adjusted under 35 U.S.C. 154(b) by 0 days.

(21) Appl. No.: 10/856,751

(22) Filed: May 28, 2004

(65) Prior Publication Data

US 2005/0266414 A1 Dec. 1, 2005

(51) Int. Cl.
*C07H 21/04* (2006.01)
*C12Q 1/68* (2006.01)

(52) U.S. Cl. .................. 435/6; 435/91.1; 435/91.2; 536/23.1; 536/24.3

(58) Field of Classification Search .................. None
See application file for complete search history.

(56) References Cited

U.S. PATENT DOCUMENTS

2003/0092019 A1* 5/2003 Meyer et al. .................. 435/6

OTHER PUBLICATIONS

Laszlo, Magyar Allatorvosok LapJa (Sep. 2003, vol. 125, No. 9, abstract.*
Scmidt-Kuntzel (J. of Heredity, vol. 96, No. 4, pp. 289-301, 2005).*
Lyons et al. (Animal Genetics, vol. 36, pp. 119-126, 2005).*
Hirschhorn et al. (Genetics in Medicine. vol. 4, No. 2, pp. 45-61, Mar. 2002).*
Halaban, et al.; "Coexpression Of Wild-Type Tyrosinase Enhances Maturation Of Temperature-Sensitive Tyrosinase Mutants"; *J Invest Dermatol;* Mar. 31, 2002; pp. 481-488; vol. 119; The Society for Investigative Dermatology, Inc.; U.S.
Halaban, et al.; "Cell Biology: Tyrosinases Of Murine Melanocytes With Mutations At The Albino Locus"; *J Exp Zool;* Jun. 3, 1988; pp. 7241-7245; vol. 85; National Academy of Sciences; U.S.
Kidson and Fabian; "The Effect of Temperature on Tyrosinase Activity in Himalayan Mouse Skin"; *The Journal Of Experimental Zoology;* 1981; pp. 91-97; vol. 215; Alan R. Liss, Inc.; U.S.
King, et al.; "Temperature-sensitive Tyrosinase Associated with Peripheral Pigmentation in Oculocutaneous Albinism"; *The Journal Of Clinical Investigation;* 1991; pp. 1046-1053; vol. 87; The American Society For Clinical Investigation, Inc., U.S.
O'Brien, et al.; "Comparative Gene Mapping In The Domestic Cat (*Felis catus*)"; *The Journal Of Heredity;* 1997; pp. 408-414; vol. 88; Oxford University Press; UK.
O'Brien, et al.; "Chromosomal Mapping Of Beta-Goblin And Albino Loci In The Domestic Cat"; *The Journal Of Heredity;* 1986; pp. 374-378; vol. 77, Oxford University Press; UK.
Rinchik, et al.; "Molecular Analysis Of Radiation-Induced Albino ©-Locus Mutations That Cause Death at Preimplantation Stages of Development"; *Genetics;* 1993; pp. 1107-1116; vol. 135; TheGenetics Society of America; U.S.
Robinson; "Acromelanic Albinism in Mammals"; *Genetica;* 1973; pp. 454-458; vol. 44; Kluwer Academic Publishers; Germany.
Schumtz et al., "*Canis familiaris* Tyrosinase mRNA," Genbank Accession No. AY336053, Jan. 2004.
International Search Report issued by the PCT office for corresponding PCT application No. PCT/US05/11931 filed Apr. 8, 2005.

* cited by examiner

*Primary Examiner*—Jeanine A. Goldberg

(57) ABSTRACT

The present invention provides compositions and methods for detecting mutations associated with albinism in the cat.

11 Claims, 8 Drawing Sheets

Figure 1

Fig. 1A
```
CCTTGGCACAGACTCTTCTTGTTGCTGTGGGAACAAGAAATCCAGAAGCTGACCGGGGAT Majority
---------+---------+---------+---------+---------+---------+
...............T........AT.................T.GAG.A..A..T...... Mmus
.............................................A...... Ocun
............................................................ Cfam
............................................................ Fcat wt
......................................................T..... Fcat Bu
............................................................ Fcat Pe
```

Fig. 1B
```
LGGSEIWKDIDFAHEAPGFLPWHRLFLLLWEQEIQKLTGDENFTIPYWDWRDAKSCDICT Majority
---------+---------+---------+---------+---------+---------+
.......R......................RE........V........EN..... Mmus
.....V.R.......................................E...V.. Ocun
............................................................ Cfam
............................................................ Fcat wt
...........................................W................ Fcat Bu
............................................................ Fcat Pe
```

Fig. 1C
```
GCGCAATCCTGGAAACCATGACAAAGCCAGGACCCCAAGGCTCCCCTCCTCTGCTGATGT Majority
+---------+---------+---------+---------+---------+---------
A..T....................AA.....C........A..T..A..A..... Mmus
.....................T..G................AT.A..... Ocun
............G..........................A.................... Cfam
.........C.................................................. Fcat wt
.........C.................................................. Fcat Bu
.........CA.................................................. Fcat Pe
.........C...........................................-...... Fcat alb
```

Fig. 1D
```
CDGTPEGPLLRNPGNHDKARTPRLPSSADVEFCLSLTQYESGSMDKAA Majority
---------+---------+---------+---------+---------+-
................K..........................RT. Mmus
.NA.S................S...................... Ocun
...................................D...... Cfam
............................................ Fcat wt
............................................ Fcat Bu
............R............................... Fcat Pe
.....................PLLMWN.A.V.HNMNRVPWI.LH Fcat alb
```

Figure 2

Table 1. PCR analysis of *TYR* in the domestic cat.

| Exon | Exon Size (bp) | Product Size (bp) | Forward Primer Reverse Primer | Exon Sequenced* |
|---|---|---|---|---|
| 1 | 1321 | 785 | ctgcctgctgtggagtttc agaatgatgctgggctgagt | 746/1321 (56%) |
| 2 | 217 | 180 | tagccgattggaggatacaa gcagctttatccatggaacc | 139/217 (64%) |
| 3 | 148 | 127 | cttactgggatagcggatgc caaatgcatggtgaagaagg | 87/148 (59%) |
| 4 | 182 | 175 | tatttttgagcagtggctcc ttgtagatagctatagtcatagcccag | 128/182 (70%) |
| 5 | 516 | 193 | tcagacccagactcttttcaag ctttctccatgaggagtggc | 0/516 (0%) |

*Product length excluding primer sequence

Figure 3

SEQ ID NO:1
Exon 1 Variant - Burmese phenotype

AGCCTGATGGAGAAGGAATGCTGTCCAGCGTGGACGGGTGACAGCAGTCCCTGCGGCCAGCTCTCAGGCAGGGGT
GCCTGTCAGGACATCACGCTGTCCAAAGCTCCACTCGGGCCTCAATACCCCTTCACGGGGATGGATGACCGGGAG
GCCTGGCCCTCCGTCTTTTATAATCGGACCTGCCAGTGCTTTGGCAACTTCATGGGATTCAACTGTGGAAATTGC
AAGTTTGGCTTTTGGGGACCAAACTGCACAGAGAAGCGACTTTTGGTGAGAAGAAACATCTTTGATTTGAGCGTC
CCAGAGAAGAACAAATTTCTTGCCTACCTCACTTTAGCGAAGCATACTATCAGCCCAGACTATGTCATCCCCATA
GGCACCTATGGCCAAATGAATAATGGATCTACACCCATGTTTAATGACATCAATGTTTATGACCTCTTCGTCTGG
ATGCATTACTATGTGTCAAGGGACACACTGCTTGGAGGGTCTGAAATCTGGAAAGACATTGATTTTGCTCATGAA
GCCCCTGGTTTCCTGCCTTGGCACAGACTCTTCTTGTTGCTGTGGGAACAAGAAATCCAGAAGCTGACC(T)GGG
ATGAGAACTTCACTATTCCATATTGGGATTGGCGAGATGCTAAAAGCTGTGACATTTGCACAGATGAGTACATGG
GAGGG

SEQ ID NO:40
Exon 2 Variant - Siamese phenotype

TAGCCGATTGGAGGAGTACAATAGCCGTCAGGCTTTATGTGATGGAACTCCAGAGGGACCATTACTGCGCAATCC
C(A)GAAACCATGACAAAGCCAGGACCCCAAGGCTCCCCTCCTCTGCTGATGTGGAATTTTGCCTAAGTCTGACA
CAATATGAATCGGGTTCCATGGATAAAGCTGC

SEQ ID NO:41
Exon 2 Variant - Albino phenotype

TAGCCGATTGGAGGAGTACAATAGCCGTCAGGCTTTATGTGATGGAACTCCAGAGGGACCATTACTGCGCAATCC
CGGAAACCATGACAAAGCCAGGACCCCAAGGCTCCC(c)TCCTCTGCTGATGTGGAATTTTGCCTAAGTCTGACA
CAATATGAATCGGGTTCCATGGATAAAGCTGC

Figure 4

AY012029.
tyrosinase
Felis catus

```
  1 gcctgtcagg acatcacgct gtccaaagct ccactcgggc ctcaataccc cttcacgggg
 61 atggatgacc gggaggcctg gccctccgtc ttttataatc ggacctgcca gtgctttggc
121 aacttcatgg gattcaactg tggaaattgc aagtttggct tttggggacc aaactgcaca
181 gagaagcgac ttttggtgag aagaaacatc tttgatttga gcgtcccaga gaagaacaaa
241 tttcttgcct acctcacttt agcgaagcat actatcagcc cagactatgt catccccata
301 ggcacctatg ccaaatgaa taatggatct acacccatgt ttaatgacat caatgtttat
361 gacctcttcg tctggatgca ttactatgtg tcaagggaca cactgcttgg agggtctgaa
421 atctgg
```

Figure 5

U40716
tyrosinase
Felis catus

```
  1 gattggagga gtacaatagc cgtcaggctt tatgtgatgg aactccagag ggaccattac
 61 tgcgcaatcc cggaaaccat gacaaagcca ggaccccaag gctcccctcc tctgctgatg
121 tggaattttg cctaagtctg acacaatatg aatcggattc catggataaa gctgccaatt
181 tcagctttag gaatacactg gaaggatttg ctagtccact tactgggata gcagatgcct
241 ctca
```

Figure 6

AAG38772
142 aa
Felis catus
tyrosinase

```
  1 acqditlska plgpqypftg mddreawpsv fynrtcqcfg nfmgfncgnc kfgfwgpnct
 61 ekrllvrrni fdlsvpeknk flayltlakh tispdyvipi gtygqmnngs tpmfndinvy
121 dlfvwmhyyv srdtllggse iw
```

Figure 7

AAB08729
tyrosinase
Felis catus
       1 leeynsrqal cdgtpegpll rnpgnhdkar tprlpssadv efclsltqye sdsmdkaanf
      61 sfrntlegfa spltgiadas

Figure 8

AY336053
*Canis familiaris* tyrosinase (TYR) mRNA, complete cds.

```
   1 tttcctgcag accttgtgag gactagagga agaagaatgc tcctggctgc tttgtgctgt
  61 ctgctgtgga gtttccgaac ctccactggc catttccctc gagcctgtgc ctcctccaag
 121 agcctgatgg agaaggaatg ctgcccacca tggagtggtg acgggagtcc ctgtggccag
 181 ctttcaggca ggggtgcctg tcaggacatc atactatcca atgcccatt cgggcctcag
 241 ttccccttca cgggggtgga tgaccgggaa tcttggcctt ctgtctttta caatcggacc
 301 tgccagtgct ttggtaactt catgggattc aactgtggaa attgcaagtt tggcttttgg
 361 ggacaaaact gcacagagaa gcgacttttg gtgagaaaaa acatctttga tttgagtgtc
 421 ccagagaaga acaaatttct tgcctacctt actttagcaa agcatactac cagcccagac
 481 tatgtcatcc ccacaggtac ctatggccaa atgaataatg gatcaacacc catgtttaat
 541 gacatcaaca tttatgatct ctttgtctgg atgcattatt atgtgtcaag ggacacactg
 601 cttggagggt ctgaaatctg gaaagacatt gattttgctc atgaagcccc aggtttcctg
 661 ccttggcaca gactcttcct gttgctgtgg gaacaagaaa tccagaagct gaccggggat
 721 gagaacttca ctattccata ttgggattgg cgagatgcta aaagctgtga catttgcaca
 781 gatgagtaca tgggagggcg caacccagca aacccaaaac tactcagccc agcatccttc
 841 ttctcctctt ggcagatcgt ctgcacccga ctggaggagt acaacagccg acaggcttta
 901 tgcgatggaa ctccagaagg accgttactg cgcaatcctg ggaaccatga caaagccagg
 961 accccaagac tcccctcctc tgctgatgtg gaattctgcc tgagtctgac ccagtatgaa
1021 tcggattcca tggataaagc tgccaatttc agctttagaa atacactgga aggatttgct
1081 agtccactta ctgggatagc agatgcctct caaagcagta tgcacaatgc cttgcatatc
1141 tatatgaatg gaacaatgtc tcaggtaccg ggatctgcca atgatcccat ttttcttctt
1201 caccatgcat tcgttgacag tattttttgag cagtggctcc gaaggcacca tcctcttcga
1261 gaagtttatc cagaagccaa tgctcctatt ggacacaacc gggaatccta catggttcct
1321 tttatacctc tgtacagaaa tggtgatctc tttatttcat ccagagatct gggctatgac
1381 tatagcaacc tacaagaatc agaacgggac attttttcaag attacattaa gccctactta
1441 gaacaagcaa gtcggatctg gccatggctc attggggctg ctgtggtagg ctgtgtcgtc
1501 actgctgtgc taggagggct caccagccta ttgtgtcggc gcaatagaaa gcagctccat
1561 gaagaaaagc agccactcct catggaaaag gaggattacc acagcttgtt gtatcagacc
1621 catctataaa aggcttaggc aatagagtag ggccaaa
``` ately one color variant are not recognized. For
CARRIER TESTS FOR ALBINISM IN THE CAT

CROSS-REFERENCES TO RELATED APPLICATIONS

Not applicable

STATEMENT AS TO RIGHTS TO INVENTIONS MADE UNDER FEDERALLY SPONSORED RESEARCH OR DEVELOPMENT

Not application

BACKGROUND OF THE INVENTION

Albinism has been recognized in many mammalian species including humans. In man, at least 72 entries are cataloged in Mendelian Inheritance in Man and have been shown to cause various forms of albinism. Albinism is associated with other medical conditions, such as deafness and immunodeficiencies, thus, albinism mutations, which affect melanocyte production and migration, also have pleiotrophic effects that present as vision, auditory and other abnormalities (Brown et al., 1971; Creel et al., 1983; Elekessy et al., 1973; Guillery, 1974; Guillery, 1996; Guillery et al., 1974; Halaban et al., 1988; Leventhal et al., 1985; Weber et al., 1978). Hence, the genes controlling pigmentation play other important physiological roles in mammalian biology besides coloration and potential UV protection.

The domestic cat has at least three loci (dominant white, white spotting, pointing) controlling pigment production that include genes that affect melanocyte production and migration and melanin synthesis. Dominant white, W, affects melanocyte production and is strongly associated with eye color and deafness (Bamber, 1933; Bergsma et al., 1971; Brown et al., 1971). White spotting, S, affects melanocyte migration and produces cats with mainly dorsal pigmentation (Kuhn, 1928; Whiting, 1919). Tentative alleles at the S locus can be expressed as white feet only, white belly or neck spots, or, in the homozygous state, SS, patches of color only near the ears and on the tail. The tyrosinase gene, TYR, which encodes an enzyme required for melanin production in mammals (Halaban et al., 2002; Robinson, 1973) has been implicated for several decades as the gene controlling Siamese "points" ($c^s$). The tyrosinase locus was originally designated the Color locus, C, and was later assigned as the causative gene for temperature sensitive and albinism mutations in several species, excluding the cat.

Albinism variations have been recognized in the domestic cat for several hundred years. The Siamese cat, one of the originally developed cat breeds, has a distinguishing phenotype that is a form of albinism. Siamese cats have a distinctive coat color with pigment only being found on the cooler extremities of the body, producing a "mask" on the face and darkened paws and tail. This type of albinism is commonly referred to as "pointed" or "himalayan" in non-human species and has been recognized in rabbits, gerbil and humans (Aigner et al., 2000; Petrij et al., 2001; Tripathi et al., 1991). Since, the causative mutations have been determined or are linked to the gene tyrosinase (TYR) in these other species, the cat phenotypes have also been suggested to be a result of temperature-sensitive mutations at the same gene (Halaban et al., 2002; Kidson et al., 1981; King et al., 1991). A linkage analysis between the Siamese "pointed" phenotype and protein polymorphisms in hemoglobin, HBB, which is closely linked to TYR, also supported this conclusion (O'Brien et al., 1986). At that time, linkage had been shown between HBB and TYR in various species, but only proven to be syntenic in the cat via a somatic cell hybrid panel (O'Brien et al., 1997 and Rinchik et al., 1993), but the Siamese and Burmese phenotype mutations in cats were not been previously determined, nor were albino cats definitively been proven to be a mutation of the TYR albinism series.

Cats have been proven to have an allelic series with at least three alleles, $C > c^b >$, $c^s$ (Thompson, 1943; Tjebbes, 1942). These three alleles produce four phenotypes: C allele is completely dominant with normal color presentation; the Burmese phenotypic variant, $c^b c^b$, expresses as sable coloration throughout the body and extremities, although all pigment is black (eumelanin); the Siamese phenotypic variant; $c^s c^s$, is the "pointed" coloration with blue eyes, which only has pigment production at the cooler areas, the face, ears, paws, and tail; and the Tonkinese phenotypic variant, $c^b c^s$, which is an intermediate between the Burmese and Siamese. Several cat breeds are fixed for the albinism alleles, which include Burmese and Singapura for the $c^b$ allele, and Siamese, Birman and Himylayan for the $c^s$ allele.

Albino cats have been sporadically mentioned in the literature but quality photographs are not available nor has the phenotype been proven to be allelic to the color series (Turner et al., 1981). Also, blue-eyed versus pinked-eyed albino cats have not been clearly distinguished in published reports (Todd, 1977; Turner et al., 1981), thus it is unclear as to whether there are more than one complete albinism alleles in the cat, as has been reported for the mouse. Robinson (1973) suggested that albino cats would be an allele of TYR due to other species also showing the same phenotype with known mutations. Breeding experiments with Siamese type cats were attempted but did not produce an albino cat because the breeding study had to be terminated. Over 300 albino cats have been registered by the Cat Fanciers' Association (CFA) as a color variant of the Siamese.

In the United States there are approximately 50 cat breeds, some of which are hybrids with wildcat species and long-haired and short-haired varieties of the same breed. Not all breeds or colors are accepted by different cat fancy organizations, but basically there are four breeds (Siamese, Birman, Balinese and Javanese) that are fixed for "Siamese" points, and three breeds (Burmese, European Burmese and Singapura) that are fixed for the Burmese allele. Tonkinese cats are heterozygotes for these two alleles, hence matings produce $c^b c^b$ Tonkinese, known as minks, and $c^s c^s$ Tonkinese that are known as color points. But due to the variations on pigment intensity due to environment, dilution factors of other genes and minor polygenic effects, distinguishing the variant of Tonkinese produced can be challenging for breeders.

Approximately thirteen breeds have desirable segregation for the $c^s$ and/or $c^b$ alleles but a few have these alleles in the gene pool but the color variants are not recognized. For example, Korats are recognized in only one color, blue, but $c^s$ segregates in this breed, producing undesirable "pointed" cats. This breed has a very limited population size, thus, the eradication of cats that have only a single gene that is undesirable, point-restriction, but many that contribute positively to the breed, could be very detrimental to the genetic diversity of the population. Hence, genetic tests for undesirable single gene traits could allow the continued management of the allele within the population, but through carrier testing, matings could be established that do not breed carrier to carrier, which would produced 25% undesirable cats.

Cat breeders fear undesirable traits, which quenches the enthusiasm for opening stud books and allowing the outcrossing of many domesticated breeds. Genetic testing for some of the undesirable traits, including albinism, can alleviate some of these fears and can promote better genetic diversity, increased heterozygosity, and hence possibly overall better health for companion animal breeds as well as animal breeds in captive breeding programs.

Thus, there is a need in the art for methods and compositions for testing for undesirable traits, including albinism. The present invention satisfies these and other needs.

BRIEF SUMMARY OF THE INVENTION

One embodiment of the present invention provides isolated polynucleotides comprising the sequence provided in SEQ ID NOS:1, 2, 3 or a complement thereof. In some embodiments, the invention provides expression vectors comprising a polynucleotide comprising the sequence provided in SEQ ID NOS: 1, 2, 3 or a complement thereof, operably linked to an expression control sequence and host cells comprising the expression vector. The host cell may be a mammalian cell, a yeast cell, or a bacterial cell (e.g., *E. coli*). In some embodiments, the invention provides polypeptides comprising an amino acid sequence encoded by Another embodiment of the invention provides methods for detecting a mutation associated with albinism in a cat by detecting a subsequence of a nucleic acid encoding TYR, the subsequence comprising a G to T substitution at position 715 of exon 1 of TYR, a G to A substitution in exon 2 at position 940 of TYR (canine reference sequence AYAY336053), or a C deletion in exon 2 at position 975 of TYR (canine reference sequence AYAY336053) in a biological sample from the cat. The subsequence may comprise SEQ ID NOS:1, 2, 3 or complements thereof. The cat may be a domesticated cat or a feral cat. In some embodiments, the mutation is detected by specifically amplifying the subsequence comprising position 715 of exon 1 of TYR, exon 2 at position 940 of a nucleic acid encoding TYR, or exon 2 at position 975 of a nucleic acid encoding TYR, or combinations thereof, in the biological sample from the cat, thereby amplifying nucleic acids comprising the mutation (e.g., nucleic acids comprising a G to T substitution at position 715 of exon 1 of TYR, a G to A substitution exon 2 at position 940 of TYR, or a C deletion in exon 2 at position 975 of TYR); and detecting the amplified nucleic acids, thereby detecting the mutation. The subsequence may comprise SEQ ID NOS:1, 2, 3 or complements thereof. The nucleic acids may be specifically amplified using primers comprising the sequences set forth in SEQ ID NOS: 4 and 5 or 6 and 7. The mutation may be detected by contacting the amplified nucleic acids with a restriction enzyme (e.g., Hpa II), by sequencing, or a combination thereof. In some embodiments, the amplified nucleic acids are detected by sequencing. In some embodiments the mutation is detected by contacting an antibody that specifically binds to a polypeptide encoded subsequence of a gene encoding TYR, wherein the subsequence comprises a G to T substitution at position 715 of exon 1 of TYR, a G to A substitution exon 2 at position 940 of TYR, or a C deletion in exon 2 at position 975 of TYR, with the biological sample from the cat, thereby forming a complex between the antibody and a polypeptide in the sample; and detecting the presence of the complex, thereby detecting the mutation. The subsequence may comprise SEQ ID NOS:1, 2, 3 or complements thereof. In some embodiments, the complex may be further contacted with an Ig-specific antibody. The Ig-specific antibody may be labeled with a detectable label (e.g., an isotope or a fluorescent label).

A further embodiment of the invention provides kits for detecting a mutation associated with albinism. In some cases the kits comprise an isolated polynucleotide comprising a subsequence of a gene encoding TYR, the subsequence comprising a G to T substitution at position 715 of exon 1 of TYR, a G to A substitution exon 2 at position 940 of TYR, or a C deletion in exon 2 at position 975 of TYR; and primers that specifically amplify the subsequence. The subsequence may comprise SEQ ID NOS:1, 2, 3 or complements thereof. The primers may comprise the sequences set forth in SEQ ID NOS: 4 and 5 or 6 and 7. The kits may further comprise a restriction enzyme (e.g., Mly I). In some cases the kits comprise an antibody that specifically binds to a polypeptide encoded by a subsequence of a gene encoding TYR wherein the subsequence comprises a G to T substitution at position 715 of exon 1 of TYR, a G to A substitution exon 2 at position 940 of TYR, or a C deletion in exon 2 at position 975 of TYR. The subsequence may comprise SEQ ID NOS:1, 2, 3 or complements thereof. The kits may further comprise a Ig-specific antibody. The Ig-specific antibody may be labeled with a detectable label (e.g., an isotope or a fluorescent label).

Even another embodiment of the invention provides isolated polynucleotides capable of distinguishing between the sequence provided in SEQ ID NOS:1, 2, 3 or complements thereof and a nucleic acid encoding a wild type tyrosinase protein.

BRIEF DESCRIPTION OF THE DRAWINGS

FIG. 1 shows the sequence alignment of feline tyrosinase (TYR) and amino acid translation as compared to species exhibiting albinism. Species used include: *Mmus*:mouse, *Ocun*:rabbit, *Cfam*:dog and representative *Fcat*:cat samples (wildtype:wt, Burmese:Bu, Persian:Pe and albino:alb). FIG. 1A shows DNA sequence alignment (SEQ ID NOS:14–17) of exon 1 with the Burmese mutation in bold. FIG. 1B shows protein translation (SEQ ID NOS:18–21) of exon 1 with the Burmese mutation in bold. FIG. 1C shows DNA sequence (SEQ ID NOS:22–28) alignment of exon 2 with the Siamese mutation in bold. The—indicates a missing nucleotide. FIG. 1D shows protein translation (SEQ ID NOS:29–34) of exon 2 with the Siamese mutation in bold. The frame-shift caused by the albino mutation is evident.

FIG. 2 is Table 1 which summarizes the results of PCR analysis of TYR (i.e., of exons 1, 2, 3, 4, and 5) in the domestic cat and primer sequences (SEQ ID NOS:4–13) used for the analysis.

FIG. 3 shows SEQ ID NOS:1, 40, and 41. SEQ ID NO:1 comprises the G to T substitution (bold) in exon 1; SEQ ID NO:40 comprises the G to A substitution (bold) exon 2; and SEQ ID NO:40 comprises the C deletion (lowercase) in exon 2.

FIG. 4 shows the sequence (SEQ ID NO:35) for Genbank Accession No. AY012029, a partial coding sequence for feline tyrosinase.

FIG. 5 shows the sequence (SEQ ID NO:36) for Genbank Accession No. U40716, a partial coding sequence for feline tyrosinase.

FIG. 6 shows the sequence for (SEQ ID NO:37) for Genbank Accession No. AAG38772, the amino acid sequence for feline tyrosinase encoded by Genbank Accession No. AY012029.

FIG. 7 shows the sequence (SEQ ID NO:38) for Genbank Accession No. AAB08729, the amino acid sequence for feline tyrosinase encoded by Genbank Accession No. U40716.

FIG. 8 shows the sequence (SEQ ID NO:39) for Genbank Accession No. AY336053, the *Canis familiaris* tyrosinase (TYR) mRNA, complete cds.

DETAILED DESCRIPTION OF THE INVENTION

I. Introduction

The present invention is based on the identification of three mutations in the feline TYR gene that are with the Siamese, Burmese, and blue-eyed albino phenotypes for the domestic cat. Sequence analysis identified a G to T substitution at position 715 of exon 1 of a gene encoding tyrosinase (TYR) which is linked to the Burmese phenotype; a G to A substitution in exon 2 at position 940 of TYR (canine reference sequence AY336053) which is linked to the Siamese phenoype, or a C deletion in exon 2 at position 975 of TYR (canine reference sequence AY336053) which is linked to the albino phenotype. Thus, a carrier test for albinism is now possible.

Thus, the invention provides compositions, methods, and kits for identifying carriers of albinism. Cats identified as carriers of albinism can be used as models for study of the disease and development of therapy for albinism. Cats identified as carriers of albinism can also be removed from breeding populations to enhance the overall health of cat breeds, both domesticated and wild; i.e., breeders could manage the mutations within the populations while maintaining needed genetic diversity. In addition, identification of these mutations can be useful in forensic settings where identification of the source of hair and other biological materials can assist in crime detection.

II. Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y.), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The terms "TYR," and "TYR" refer to nucleic acids and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by a TYR nucleic acid (for a cat TYR nucleic acid sequence, see, e.g., SEQ ID NOS: 1, 2, or 3 and FIG. 1; for an amino acid sequence of a cat TYR polypeptide see, e.g., FIG. 1); (2) bind to antibodies, e.g., polyclonal antibodies, raised against an immunogen comprising an amino acid sequence of a TYR polypeptide (e.g., encoded by SEQ ID NOS: 1, 2, or 3), and conservatively modified variants thereof, (3) specifically hybridize under stringent hybridization conditions to an anti-sense strand corresponding to a nucleic acid sequence encoding a TYR protein, and conservatively modified variants thereof, (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a TYR nucleic acid. A polynucleotide or polypeptide sequence is typically from a mammal including, but not limited to, domestic cats and wild cats (e.g., of the family Felidae; the subfamilies, Felinae, Pantherinae, and Acinonychinae; the genera *Caracal, Catopuma, Felis, Herpailurus, Leopardus, Leptailurus, Lynx, Oncifelis, Oreailurus, Otocolobus, Prionailurus, Profelis, Puma, Neofelis, Panthera, Pardofelis,* and *Uncia*; and the species *felis, lybica, jubatus, caracal, badia, bieti, chaus, margarita, nigripes, silvestris, gordonii, yaguarondi, pardalis, tigrinus, wiedi, serval, canadensis, lynx, pardinus, rufus, colocolo, geoffroyi, guigna, jacobita, manul, bengalensis, planiceps, rubiginosus, viverrinus, aurata, concolor, nebulosa, leo, onca, pardus, tigris, marmorata,* and *uncia*. The nucleic acids and proteins of the invention include both naturally occurring or recombinant molecules.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated TYR nucleic acid is separated from open reading frames that flank the TYR gene and encode proteins other than TYR. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605–2608 (1985); Rossolini et al., Mol. Cell. Probes 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or "detectable label" is a composition detectable by spectroscopic, photochemical, biochemical, immunochemical, or chemical means. For example, useful labels include radioisotopes (e.g., $^3$H, $^{35}$S, $^{32}$P, $^{51}$Cr, or $^{125}$I), fluorescent dyes, electron-dense reagents, enzymes (e.g., alkaline phosphatase, horseradish peroxidase, or others commonly used in an ELISA), biotin, digoxigenin, or haptens and proteins for which antisera or monoclonal antibodies are available (e.g., the polypeptide encoded by SEQ ID NOS: 1, 2, or 3 can be made detectable, e.g., by incorporating a radiolabel into the peptide, and used to detect antibodies specifically reactive with the peptide).

An "amplification reaction" refers to any chemical reaction, including an enzymatic reaction, which results in increased copies of a template nucleic acid sequence. Amplification reactions include polymerase chain reaction (PCR) and ligase chain reaction (LCR) (see U.S. Pat. Nos. 4,683,195 and 4,683,202; *PCR Protocols: A Guide to Methods and Applications* (Innis et al., eds, 1990)), strand displacement amplification (SDA) (Walker, et al. *Nucleic Acids Res.* 20(7):1691 (1992); Walker *PCR Methods Appl* 3(1):1 (1993)), transcription-mediated amplification (Phyffer, et al., *J. Clin. Microbiol.* 34:834 (1996); Vuorinen, et al., *J. Clin. Microbiol.* 33:1856 (1995)), nucleic acid sequence-based amplification (NASBA) (Compton, *Nature* 350(6313):91 (1991), rolling circle amplification (RCA) (Lisby, *Mol.*

Biotechnol. 12(1):75 (1999)); Hatch et al., *Genet. Anal.* 15(2):35 (1999)) and branched DNA signal amplification (bDNA) (see, e.g., Iqbal et al., *Mol. Cell Probes* 13(4):315 (1999)).

"Amplifying" refers to submitting a solution to conditions sufficient to allow for amplification of a polynucleotide if all of the components of the reaction are intact. Components of an amplification reaction include, e.g., primers, a polynucleotide template, polymerase, nucleotides, and the like. Thus, an amplifying step can occur without producing a product if, for example, primers are degraded.

"Amplification reagents" refer to reagents used in an amplification reaction. These reagents can include, e.g., oligonucleotide primers; borate, phosphate, carbonate, barbital, Tris, etc. based buffers (see, U.S. Pat. No. 5,508,178); salts such as potassium or sodium chloride; magnesium; deoxynucleotide triphosphates (dNTPs); a nucleic acid polymerase such as Taq DNA polymerase; as well as DMSO; and stabilizing agents such as gelatin, bovine serum albumin, and non-ionic detergents (e.g. Tween-20).

The term "primer" refers to a nucleic acid sequence that primes the synthesis of a polynucleotide in an amplification reaction. Typically a primer comprises fewer than about 100 nucleotides and preferably comprises fewer than about 30 nucleotides. Exemplary primers range from about 5 to about 25 nucleotides. The "integrity" of a primer refers to the ability of the primer to primer an amplification reaction. For example, the integrity of a primer is typically no longer intact after degradation of the primer sequences such as by endonuclease cleavage.

The term "subsequence" refers to a sequence of nucleotides that are contiguous within a second sequence but does not include all of the nucleotides of the second sequence.

A "target" or "target sequence" refers to a single or double stranded polynucleotide sequence sought to be amplified in an amplification reaction. Two target sequences are different if they comprise non-identical polynucleotide sequences.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The terms "promoter" and "expression control sequence" are used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region such as exons 1 or 2 of the TYR gene or another region of SEQ ID NOS: 1, 2, or 3), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to TYR nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5–10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5x SSC and 1% SDS incubated at 42° C. or 5×SSC and 1% SDS incubated at 65° C., with a wash in 0.2×SSC and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.–95° C. for 30 sec–2 min., an annealing phase lasting 30 sec.–2 min., and an extension phase of about 72° C. for 1–2 min.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH—CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552–554 (1990)).

For preparation of monoclonal or polyclonal antibodies, any technique known in the art can be used (see, e.g., Kohler & Milstein, Nature 256:495–497 (1975); Kozbor et al., Immunology Today 4: 72 (1983); Cole et al., pp. 77–96 in Monoclonal Antibodies and Cancer Therapy, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348: 552–554 (1990); Marks et al., Biotechnology 10:779–783 (1992)).

An "immunogenic fragment" is one that elicits or modulates an immune response, preferably the composition induces or enhances an immune response in response to a particular TYR or a portion thereof. Immune responses include humoral immune responses and cell-mediated immune responses, such as antibody production.

An "anti-TYR" antibody is an antibody or antibody fragment that specifically binds a polypeptide encoded by a TYR gene, cDNA, or a subsequence thereof including polypeptides encoded by a mutant TYR gene, cDNA, or a-subsequence thereof, e.g., the sequences set forth in FIG. 2 or subsequences thereof.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that uses an antibody to specifically bind an antigen. The immunoassay is characterized by the use of specific binding properties of a particular antibody to isolate, target, detect, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to TYR can be selected to obtain only those polyclonal antibodies that are specifically immunoreactive with mutants of TYR (e.g., a mutant comprising a sequence encoded by SEQ ID NOS: 1, 2, or 3) and not with other proteins (e.g., wild type TYR). This selection may be achieved by subtracting out antibodies that cross-react with molecules such as TYR from other species. In addition, polyclonal antibodies raised to TYR polymorphic variants, alleles, orthologs, and conservatively modified variants can be selected to obtain only those antibodies that recognize specific fragments of TYR. For example polyclonal antibodies raised to can be selected to obtain only those antibodies that recognize polypeptides encoded by exons 1 or 2 of TYR, but not other TYR fragments. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as E. coli, or eukaryotic cells such as yeast, insect, amphibian, or mammalian cells such as CHO, HeLa and the like, e.g., cultured cells, explants, and cells in vivo.

"Biological sample" as used herein is a sample of biological tissue or fluid that is suspected of containing a nucleic acid encoding a mutant TYR polypeptide or a mutant TYR polypeptide. These samples can be tested by the methods described herein and include body fluids such as whole blood, serum, plasma, cerebrospinal fluid, urine, lymph fluids, and various external secretions of the respiratory, intestinal and genitourinary tracts, tears, saliva, milk, white blood cells, myelomas, and the like; and biological fluids such as cell extracts, cell culture supernatants; fixed tissue specimens; and fixed cell specimens. Biological samples may also include sections of tissues such as biopsy and autopsy samples or frozen sections taken for histologic purposes. These samples are well known in the art. A biological sample is obtained from any mammal including, e.g., a cat. A biological sample may be suspended or dissolved in liquid materials such as buffers, extractants, solvents and the like.

III. Nucleic Acids Encoding Mutant TYR

A. General Recombinant DNA Methods

This invention relies on routine techniques in the field of recombinant genetics. Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, Tetrahedron Letts. 22:1859–1862 (1981), using an automated synthesizer, as described in Van Devanter et. al., Nucleic Acids Res. 12:6159–6168 (1984). Purification of oligonucleotides is by either native acrylamide gel electrophoresis or by anion-exchange HPLC as described in Pearson & Reanier, J. Chrom. 255:137–149 (1983).

The sequence of the cloned genes and synthetic oligonucleotides can be verified after cloning using, e.g., the chain termination method for sequencing double-stranded templates of Wallace et al., Gene 16:21–26 (1981).

B. Cloning Methods for the Isolation of Nucleotide Sequences Encoding Mutants of TYR In general, the nucleic acid sequences encoding TYR and related nucleic acid sequence homologues are cloned from cDNA and genomic DNA libraries or isolated using amplification techniques with oligonucleotide primers. For example, TYR sequences are typically isolated from nucleic acid (genomic or cDNA) libraries by hybridizing with a nucleic acid probe, the sequence of which can be derived from SEQ ID NOS: 1, 2, or 3, or a subsequence thereof. TYR RNA and cDNA can be isolated from any cat.

Nucleic acids encoding TYR can also be isolated from expression libraries using antibodies as probes. Such polyclonal or monoclonal antibodies can be raised using, for example, the polypeptides encoded by the sequence of SEQ ID NOS: 1, 2, or 3.

TYR polymorphic variants, alleles, and interspecies homologues that are substantially identical to TYR can be isolated using TYR nucleic acid probes and oligonucleotides under stringent hybridization conditions, by screening libraries. Alternatively, expression libraries can be used to clone TYR polymorphic variants, alleles, and interspecies homologues, by detecting expressed homologues immunologically with antisera or purified antibodies made against the core domain of TYR which also recognize and selectively bind to the TYR homologue.

To make a cDNA library, TYR mRNA may be purified from any cat. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, Gene 25:263–269 (1983); Sambrook et al., supra; Ausubel et al., supra).

For a genomic library, the DNA is extracted from the tissue and either mechanically sheared or enzymatically digested to yield fragments of about 1–8 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, Science 196:180–182 (1977). Colony hybridization is carried out as generally described in Grunstein et al., Proc. Natl. Acad. Sci. USA., 72:3961–3965 (1975).

An alternative method of isolating TYR nucleic acids and their homologues combines the use of synthetic oligonucleotide primers and amplification of an RNA or DNA template (see U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify nucleic acid sequences of TYR directly from mRNA, from cDNA, from genomic libraries or cDNA libraries. Degenerate oligonucleotides can be designed to amplify TYR homologues using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of TYR encoding mRNA in physiological samples, for nucleic acid sequencing, or for other purposes. Genes amplified by the PCR reaction can be purified from agarose gels and cloned into an appropriate vector.

Amplification techniques using primers can also be used to amplify and isolate TYR DNA or RNA. For example, nucleic acids encoding TYR or fragments thereof may be obtained by amplification of a cat cDNA library or reverse transcribed from cat RNA using isolated nucleic acid primer pairs having the following sequences: 5' primer: CTGCCTGCTGTGGAGTTTC (SEQ ID NO:4) and 3' primer AGAATGATGCTGGGCTGAGT (SEQ ID NO:5) (exon 1); 5' primer: TAGCCGATTGGAGGATACAA (SEQ ID NO:6) and 3' primer: GCAGCTTTATCCATGGAACC (SEQ ID NO:7) (exon 2); 5' primer: CTTACTGGGATAGCGGATGC (SEQ ID NO:8) and 3' primer: CAAATGCATGGTGAAGAAGG (SEQ ID NO:9) (exon 3); 5' primer: TATTTTTGAGCAGTGGCTCC (SEQ ID NO:1O) and 3' primer: TTGTAGATAGCTATAGTCATAGCCCAG (SEQ ID NO:11) (exon 4); 5' primer: TCAGACCCAGACTCTTTTCAAG (SEQ ID NO:12) and 3' primer: CTTTCTCCATGAGGAGTGGC (SEQ ID NO:13' ) (exon 5).

These primers can be used, e.g., to amplify either the full length sequence or a probe of one to several hundred nucleotides, which is then used to screen a cDNA library for full-length TYR.

Gene expression of TYR can also be analyzed by techniques known in the art, e.g., reverse transcription and amplification of mRNA, isolation of total RNA or poly A+ RNA, northern blotting, dot blotting, in situ hybridization, RNase protection, probing DNA microchip arrays, and the like.

Synthetic oligonucleotides can be used to construct recombinant TYR genes for use as probes or for expression of protein. This method is performed using a series of overlapping oligonucleotides usually 40–120 bp in length, representing both the sense and non-sense strands of the gene. These DNA fragments are then annealed, ligated and cloned. Alternatively, amplification techniques can be used with precise primers to amplify a specific subsequence of the TYR gene. The specific subsequence is then ligated into an expression vector. TYR chimeras can be made, which combine, e.g., a portion of TYR with a portion of a heterologous TYR to create a chimeric, functional TYR.

The gene for TYR is typically cloned into intermediate vectors before transformation into prokaryotic or eukaryotic cells for replication and/or expression. These intermediate vectors are typically prokaryote vectors, e.g., plasmids, or shuttle vectors. Isolated nucleic acids encoding TYR proteins comprise a nucleic acid sequence encoding a TYR protein and subsequences, interspecies homologues, alleles and polymorphic variants thereof. In preferred embodiments, the isolated nucleic acid encoding a TYR protein is SEQ ID NOS: 1, 2, or 3 or a complement thereof.

C. Expression of TYR in Prokaryotes and Eukaryotes

To obtain high level expression of a cloned gene, such as those cDNAs encoding TYR, one typically subclones TYR into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the TYR protein are available in, e.g., *E. coli, Bacillus* sp., and *Salmonella* (Palva et al., Gene 22:229–235 (1983); Mosbach et al., Nature 302:543–545 (1983). Kits for such expression systems are commercially available. Eukaryotic expression systems for mammalian cells, yeast, and insect cells are well known in the art and are also commercially available.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the TYR encoding nucleic acid in host cells. A typical expression cassette thus contains a promoter operably linked to the nucleic acid sequence encoding TYR and signals required for efficient polyadenylation of the transcript, ribosome binding sites, and translation termination. The nucleic acid sequence encoding TYR may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a TYR encoding sequence under the direction of the polyhedrin promoter or other strong baculovirus promoters.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of TYR protein, which are then purified using standard techniques (see, e.g., Colley et al., J. Biol. Chem. 264:17619–17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349–351 (1977); Clark-Curtiss & Curtiss, Methods in Enzymology 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing TYR.

After the expression vector is introduced into the cells, the transfected cells are cultured under conditions favoring expression of TYR, which is recovered from the culture using standard techniques identified below.

D. Purification of TYR Protein

Either naturally occurring or recombinant TYR can be purified for use in functional assays. Naturally occurring TYR are purified, e.g., from cat and any other source of a TYR homologue. Recombinant TYR is purified from any suitable expression system.

TYR may be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., supra; and Sambrook et al., supra).

A number of procedures can be employed when recombinant TYR is being purified. For example, proteins having established molecular adhesion properties can be reversible fused to TYR. With the appropriate ligand, TYR can be selectively adsorbed to a purification column and then freed from the column in a relatively pure form. The fused protein is then removed by enzymatic activity. Finally TYR could be purified using immunoaffinity columns.

1. Purification of TYR From Recombinant Bacteria

Recombinant proteins are expressed by transformed bacteria in large amounts, typically after promoter induction; but expression can be constitutive. Promoter induction with IPTG is a one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of TYR inclusion bodies. For example, purification of inclusion bodies typically involves the extraction, separation and/or purification of inclusion bodies by disruption of bacterial cells, e.g., by incubation in a buffer of 50 mM Tris/HCl pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. TYR is separated from other bacterial proteins by standard separation techniques, e.g., with Ni-NTA agarose resin.

Alternatively, it is possible to purify TYR from bacteria periplasm. After lysis of the bacteria, when TYR is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

E. Standard Protein Separation Techniques For Purifying TYR

1. Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

2. Size Differential Filtration

The molecular weight of TYR can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

TYR can also be separated from other proteins on the basis of their size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Alternatively, YR protein can be expressed transiently in a cell by introducing into a cell an RNA encoding the TYR protein. The RNA is transcribed in vitro according to standard procedures and then introduced into a cell (e.g. such as *Xenopus oocytes*, CHO, and HeLa cells) by means such as injection or electroporation. The RNA then expresses the TYR protein.

IV. Detection of TYR Nucleic Acid Sequences

Determination of the presence of absence of a particular mutant TYR gene is generally performed by analyzing a nucleic acid sample that is obtained from a cat (e.g., of the genus *felis, panthera, neofelis*, or *acinonyx*) to be analyzed. Often, the nucleic acid sample comprises genomic DNA. It is also possible to analyze RNA samples for the presence of TYR mutations.

Detection techniques for evaluating nucleic acids for the presence of a single base change involve procedures well known in the field of molecular genetics. Further, many of the methods involve amplification of nucleic acids. Ample guidance for performing the methods is provided in the art. Exemplary references include manuals such as PCR Technology: PRINCIPLES AND APPLICATIONS FOR DNA AMPLIFICATION (ed. H. A. Erlich, Freeman Press, NY, N.Y., 1992); PCR PROTOCOLS: A GUIDE TO METHODS AND APPLICATIONS (eds. Innis, et al., Academic Press, San Diego, Calif., 1990); CURRENT PROTOCOLS IN MOLECULAR BIOLOGY, Ausubel, 1994–1999, including supplemental updates through April 2004; Sambrook & Russell, *Molecular Cloning, A Laboratory Manual* (3rd Ed, 2001).

Methods for detecting single base changes well known in the art often entail one of several general protocols: hybridization using sequence-specific oligonucleotides, primer extension, sequence-specific ligation, sequencing, or electrophoretic separation techniques, e.g., singled-stranded conformational polymorphism (SSCP) and heteroduplex analysis. Exemplary assays include 5' nuclease assays, template-directed dye-terminator incorporation, molecular beacon allele-specific oligonucleotide assays, single-base extension assays, and SNP scoring by real-time pyrophosphate sequences. Analysis of amplified sequences can be performed using various technologies such as microchips, fluorescence polarization assays, and matrix-assisted laser desorption ionization (MALDI) mass spectrometry. In addition to these frequently used methodologies for analysis of nucleic acid samples to detect single base changes, any method known in the art can be used to detect the presence of the TYR mutations described herein.

Although the methods typically employ PCR steps, other amplification protocols may also be used. Suitable amplification methods include ligase chain reaction (see, e.g., Wu & Wallace, *Genomics* 4:560–569, 1988); strand displacement assay (see, e.g., Walker et al., *Proc. Natl. Acad. Sci. USA* 89:392–396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., *Proc. Natl. Acad. Sci. USA* 86:1173–1177, 1989); and self-sustained sequence replication (3SR) (Guatelli et al., *Proc. Natl. Acad. Sci. USA* 87:1874–1878, 1990; WO 92/08800). Alternatively, methods that amplify the probe to detectable levels can be used, such as Qβ-replicase amplification (Kramer & Lizardi, *Nature* 339:401–402, 1989; Lomeli et al., *Clin. Chem.* 35:1826–1831, 1989). A review of known amplification methods is provided, for example, by Abramson and Myers in *Current Opinion in Biotechnology* 4:41–47, 1993.

In some embodiments, the mutant TYR is detected using oligonucleotide primers and/or probes. Oligonucleotides can be prepared by any suitable method, including chemical synthesis. Oligonucleotides can be synthesized using commercially available reagents and instruments. Alternatively, they can be purchased through commercial sources. Methods of synthesizing oligonucleotides are well known in the art (see, e.g, Narang et al., *Meth. Enzymol.* 68:90–99, 1979; Brown et al., *Meth. Enzymol.* 68:109–151, 1979; Beaucage et al., *Tetrahedron Lett.* 22:1859–1862, 1981; and the solid support method of U.S. Pat. No. 4,458,066).

A. PCR Identification of Carriers of Albinism

PCR can be used to detect carriers of albinism by amplification of nucleic acids encoding TYR. A general overview of the applicable technology can be found in PCR Protocols: A Guide to Methods and Applications (Innis et al. eds. (1990)) and PCR Technology: Principles and Applications for DNA Amplification (Erlich, ed. (1992)). In addition, amplification technology is described in U.S. Pat. Nos. 4,683,195 and 4,683,202.

PCR permits the copying, and resultant amplification of a target nucleic acid, e.g., a nucleic acid encoding TYR. Briefly, a target nucleic acid, e.g. DNA from a biological sample from a subject (e.g., a cat suspected of being an albinism carrier), is combined with a sense and antisense primers, dNTPs, DNA polymerase and other reaction components. (See, Innis et al., supra) The sense primer can anneal to the antisense strand of a DNA sequence of interest. The antisense primer can anneal to the sense strand of the DNA sequence, downstream of the location where the sense primer anneals to the DNA target. In the first round of amplification, the DNA polymerase extends the antisense and sense primers that are annealed to the target nucleic acid. The first strands are synthesized as long strands of indiscriminate length. In the second round of amplification, the antisense and sense primers anneal to the parent target nucleic acid and to the complementary sequences on the long strands. The DNA polymerase then extends the annealed primers to form strands of discrete length that are complementary to each other. The subsequent rounds serve to predominantly amplify the DNA molecules of the discrete length.

In general, PCR and other methods of amplification use primers which anneal to either end of the DNA of interest. For example, nucleic acids encoding mutant TYR or fragments thereof may be amplified using isolated nucleic acid primer pairs having the following sequences: 5' primer: CTGCCTGCTGTGGAGTTTC (SEQ ID NO:4) and 3' primer AGAATGATGCTGGGCTGAGT (SEQ ID NO:5) (exon 1); and 5' primer: TAGCCGATTGGAGGATACAA (SEQ ID NO:6) and 3' primer: GCAGCTTTATCCATGGAACC (SEQ ID NO:7) (exon 2). Amplification of DNA encoding mutant TYR from a biological sample from a subject suspected of being an albinism carrier indicates that the subject is a carrier for albinism.

Target nucleic acid sequences may be double or single-stranded DNA or RNA from any biological sample from a subject suspected of being an albinism carrier. Preferably, the target template is an isolated DNA sequence. Target DNA sequences may be isolated using a variety of techniques. For example, methods are known for lysing organisms and preparing extracts or purifying DNA. See, Current Protocols in Molecular Biology Volumes 1–3, John Wiley & Sons, Inc. (Ausubel et al., eds., 1994–1998) (hereinafter "Ausubel et al."). Also, total RNA or polyA+RNA can be reverse transcribed to produce cDNA that can serve as the target DNA.

B. Reaction Components

1. Oligonucleotides

The oligonucleotides that are used in the present invention as well as oligonucleotides designed to detect amplification products can be chemically synthesized, as described above. These oligonucleotides can be labeled with radioisotopes, chemiluminescent moieties, or fluorescent moieties. Such labels are useful for the characterization and detection of amplification products using the methods and compositions of the present invention.

The primer components may be present in the PCR reaction mixture at a concentration of, e.g., between 0.1 and 1.0 μM. The concentration of the target primers can be from about 0.1 to about 0.75 μM. The primer length can be between, e.g., 15–100 nucleotides in length and preferably have 40–60% G and C composition. In the choice of primer, it is preferable to have exactly matching bases at the 3' end of the primer but this requirement decreases to relatively insignificance at the 5' end. Preferably, the primers of the invention all have approximately the same melting temperature.

Typically, the primers have the following design. The most 3' portion anneals to the constant region flanking the target region to be amplified, this portion will normally have at least 6 bp of homology to the target region, preferably 9 or more bp. The region of homology is adjacent to the restriction enzyme sequence. If this recognition site is an interrupted sequence, the intervening portion of sequence between the two portions of the restriction enzyme site will normally contain bases which can anneal to the appropriate portion of the constant region flanking the target of interest. 5' to the restriction enzyme site are sufficient bases to allow the restriction enzyme to recognize its site and cleave the recognized sequence. Where the restriction enzyme site cleaves twice, once on either side of the recognition site, the primer should be sufficiently long to allow the enzyme to cleave at both of the cleavage sites. The extra nucleotides may or may not have further homology to the constant region flanking the target of interest.

2. Buffer

Buffers that may be employed are borate, phosphate, carbonate, barbital, Tris, etc. based buffers. (See, U.S. Pat. No. 5,508,178). The pH of the reaction should be maintained in the range of about 4.5 to about 9.5. (See, U.S. Pat. No. 5,508,178. The standard buffer used in amplification reactions is a Tris based buffer between 10 and 50 mM with a pH of around 8.3 to 8.8. (See Innis et al., supra.).

One of skill in the art will recognize that buffer conditions should be designed to allow for the function of all reactions of interest. Thus, buffer conditions can be designed to support the amplification reaction as well as any subsequent restriction enzyme reactions. A particular reaction buffer can be tested for its ability to support various reactions by testing the reactions both individually and in combination.

3. Salt Concentration

The concentration of salt present in the reaction can affect the ability of primers to anneal to the target nucleic acid. (See, Innis et al.). Potassium chloride is added up to a concentration of about 50 mM to the reaction mixture to promote primer annealing. Sodium chloride can also be added to promote primer annealing. (See, Innis et al.).

4. Magnesium Ion Concentration

The concentration of magnesium ion in the reaction can affect amplification of the target sequence(s). (See, Innis et al.). Primer annealing, strand denaturation, amplification specificity, primer-dimer formation, and enzyme activity are all examples of parameters that are affected by magnesium concentration. (See, Innis et al.). Amplification reactions should contain about a 0.5 to 2.5 mM magnesium concentration excess over the concentration of dNTPs. The presence of magnesium chelators in the reaction can affect the optimal magnesium concentration. A series of amplification reactions can be carried out over a range of magnesium concentrations to determine the optimal magnesium concentration. The optimal magnesium concentration can vary depending on the nature of the target nucleic acid(s) and the primers being used, among other parameters.

5. Deoxynucleotide Triphosphate Concentration

Deoxynucleotide triphosphates (dNTPs) are added to the reaction to a final concentration of about 20 μM to about 300 μM. Typically, each of the four dNTPs (G, A, C, T) are present at equivalent concentrations. (See, Innis et al.).

6. Nucleic Acid Polymerase

A variety of DNA dependent polymerases are commercially available that will function using the methods and compositions of the present invention. For example, Taq DNA Polymerase may be used to amplify target DNA sequences. The PCR assay may be carried out using as an enzyme component a source of thermostable DNA polymerase suitably comprising Taq DNA polymerase which may be the native enzyme purified from *Thermus aquaticus* and/or a genetically engineered form of the enzyme. Other commercially available polymerase enzymes include, e.g., Taq polymerases marketed by Promega or Pharmacia. Other examples of thermostable DNA polymerases that could be used in the invention include DNA polymerases obtained from, e.g., *Thermus* and *Pyrococcus* species. Concentration ranges of the polymerase may range from 1–5 units per reaction mixture. The reaction mixture is typically between 20 and 100 µl.

In some embodiments, a "hot start" polymerase can be used to prevent extension of mispriming events as the temperature of a reaction initially increases. Hot start polymerases can have, for example, heat labile adducts requiring a heat activation step (typically 95° C. for approximately 10–15 minutes) or can have an antibody associated with the polymerase to prevent activation.

7. Other Agents

Additional agents are sometimes added to the reaction to achieve the desired results. For example, DMSO can be added to the reaction, but is reported to inhibit the activity of Taq DNA Polymerase. Nevertheless, DMSO has been recommended for the amplification of multiple target sequences in the same reaction. (See, Innis et al. supra). Stabilizing agents such as gelatin, bovine serum albumin, and non-ionic detergents (e.g. Tween-20) are commonly added to amplification reactions. (See, Innis et al. supra).

C. Detection of Amplified Products

Amplified products can be detected using any means known in the art, including, e.g., restriction fragment length polymorphism (RFLP) analysis; denaturing gel electrophoresis, direct sequencing, and HPLC-based analysis.

1. RFLP Analysis

In some embodiments, a mutant TYR gene is detected using restriction fragment length polymorphism (RFLP) analysis. A subsequence of TYR is amplified from a biological sample from a cat. The amplification products are digested with a restriction enzyme. If the restriction site is present in the mutant TYR but not the wild-type TYR, the mutant sequences will be digested, but the wild type will not. Conversely if the restriction site is present in the wild-type TYR, but not the mutant TYR, the wild-type sequences will be digested, but the mutant will not. The restriction fragments are then analyzed using gel electrophoresis. Further analysis to confirm the sequence can be performed as described herein. For example, digestion of exon 2 of TYR with Hpa II leads to two fragments of 103 bp and 77 bp. Cats carrying a TYR mutation associated with the Siamese mutation lose a Hpa II site in exon 2 of TYR and cats carrying a TYR mutation associated with the Burmese mutation lose a Hpa II site in exon 1 of TYR. Nucleic acids from cats that exhibit loss of the Hpa II site can be sequenced to confirm the presence of the mutation.

2. Sequencing

The mutant TYR genes are typically detected by direct sequencing, e.g., to detect the G to T substitution at position 715 of exon 1 of TYR; a G to A substitution in exon 2 at position 940 of TYR (canine reference sequence AY336053), or a C deletion in exon 2 at position 975 of TYR or to detect the sequences set forth in SEQ ID NOS: 1, 2, or 3. Methods include e.g., dideoxy sequencing-based methods and Maxam and Gilbert sequence (see, e.g., Sambrook and Russell, supra).

3. HPLC

Target mutant TYR sequences can be differentiated using high performance liquid chromatography (HPLC) based methods including denaturing HPLC (dHPLC) as described in e.g., Premstaller and Oefner, *LC-GC Europe* 1–9 (July 2002); Bennet et al., *BMC Genetics* 2:17 (2001); Schrimi et al., *Biotechniques* 28(4):740 (2000); and Nairz et al., *PNAS USA* 99(16):10575–10580 (2002); and ion-pair reversed phase HPLC-electrospray ionization mass spectrometry (ICEMS) as described in e.g., Oberacher et al.; *Hum. Mutat.* 21(1):86 (2003).

Partially denaturing HPLC analysis compares two or more sets of amplified products (e.g., a wild-type TYR amplicon and a mutant TYR amplicon). The amplified products are denatured (e.g., at about 95° C.) and allowed to reanneal by gradually lowering the temperature from about 95° C. to about 30° C. In the presence of a TYR mutation the original homoduplex products are reformed along with heteroduplex products comprising the sense and anti-sense strands of either homoduplex. The homoduplexes and heteroduplexes are loaded onto an HPLC apparatus at a partially denaturing temperature of about 50° C. to about 70° C. and can be distinguished based on their elution profile. Completely denaturing HPLC analysis compares two or more sets of amplicons (e.g., primer extension products). The amplified products are loaded onto an HPLC apparatus at a completely denaturing temperature of about 70° C. to about 80° C. Specific sequence variants are eluted from the column by varying the temperature of the column and sequence variants are distinguished based on their order of elution from the column.

Ion-pair reversed phase HPLC-electrospray ionization mass spectrometry (ICEMS) uses a combination of HPLC under completely denaturing conditions and ICEMS to resolve differences between nucleic acid sequences.

4. Denaturing Gradient Gel Electrophoresis

Amplification products generated using the polymerase chain reaction can be analyzed by the use of denaturing gradient gel electrophoresis. Different TYR mutations can be identified based on the different sequence-dependent melting properties and electrophoretic migration of DNA in solution (see, e.g., Erlich, ed., PCR TECHNOLOGY, PRINCIPLES AND APPLICATIONS FOR DNA AMPLIFICATION, W. H. Freeman and Co, New York, 1992, Chapter 7).

5. Single Base Extensions

Another method for characterizing single base changes in TYR does not require use of a complete PCR, but typically uses only the extension of a primer by a single, fluorescence-labeled dideoxyribonucleic acid molecule (ddNTP) that is complementary to the nucleotide to be investigated. The nucleotide at the site of the TYR mutation can be identified via detection of a primer that has been extended by one base and is fluorescently labeled (e.g., Kobayashi et al, *Mol. Cell. Probes*, 9:175–182, 1995).

6. Single-Strand Conformation Polymorphism Analysis

Target mutant TYR sequences can be differentiated using single-strand conformation polymorphism analysis, which identifies base differences by alteration in electrophoretic migration of single stranded PCR products, as described, e.g, in Orita et al., *Proc. Nat. Acad. Sci.* 86, 2766–2770 (1989). Amplified PCR products can be generated using methods known in the art, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between wild type and mutant TYR sequences.

Methods for detecting single base changes often employ labeled oligonucleotides. Oligonucleotides can be labeled by incorporating a label detectable by spectroscopic, photochemical, biochemical, immunochemical, or chemical means. Useful labels include fluorescent dyes, radioactive labels, e.g., $^{32}$P, electron-dense reagents, enzyme, such as peroxidase or alkaline phsophatase, biotin, or haptens and proteins for which antisera or monoclonal antibodies are available. Labeling techniques are well known in the art (see, e.g., Current Protocols in Molecular Biology, supra; Sambrook & Russell, supra).

7. Sequence Specific Hybridization

A technique commonly referred to as allele specific oligonucleotide hybridization (ASO) (e.g., Stoneking et al., Am. J. Hum. Genet. 48:70–382, 1991; Saiki et al., Nature 324, 163–166, 1986; EP 235,726; and WO 89/11548) can used to detect mutant TYR genes. Two DNA molecules differing by one base are distinguished by hybridizing an oligonucleotide probe that is specific for one of the variants (e.g., wild type or mutant TYR) to an amplified product obtained from amplifying the nucleic acid sample. The probes are designed to differentially hybridize to one variant versus another. Principles and guidance for designing such probes is available in the art (see, e.g., Jeffrys and Mays, Genome Res. 13(1): 2316–2324 (2003) and Howell et al., Nature Biotech 17(1): 87–88 (1999)). Hybridization conditions should be sufficiently stringent that there is a significant difference in hybridization intensity between alleles, and preferably an essentially binary response, whereby a probe hybridizes to only one of the sequences.

The presence of a TYR mutation is determined by measuring the amount of sequence-specific oligonucleotide that is hybridized to the sample. Typically, the oligonucleotide is labeled with a label such as a fluorescent label. For example, a mutant TYR-specific oligonucleotide is applied to immobilized oligonucleotides representing TYR sequences. After stringent hybridization and washing conditions, fluorescence intensity is measured for each TYR oligonucleotide.

For example, the nucleotide present at the site of the TYR mutation is identified by hybridization under sequence-specific hybridization conditions with an oligonucleotide probe exactly complementary to a TYR mutation in a region encompassing the TYR mutation. The probe hybridizing sequence and sequence-specific hybridization conditions are selected such that a single mismatch at the mutation site destabilizes the hybridization duplex sufficiently so that it is effectively not formed. Thus, under sequence-specific hybridization conditions, stable duplexes will form only between the probe and the exactly complementary TYR sequence.

Suitable assay formats for detecting hybrids formed between probes and target nucleic acid sequences in a sample are known in the art and include the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099; each incorporated herein by reference.

In a dot-blot format, amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe. A preferred dot-blot detection assay is described in the examples.

In the reverse dot-blot (or line-blot) format, the probes are immobilized on a solid support, such as a nylon membrane or a microtiter plate. The target DNA is labeled, typically during amplification by the incorporation of labeled primers. One or both of the primers can be labeled. The membrane-probe complex is incubated with the labeled amplified target DNA under suitable hybridization conditions, unhybridized target DNA is removed by washing under suitably stringent conditions, and the membrane is monitored for the presence of bound target DNA. A preferred reverse line-blot detection assay is described in the examples.

An allele-specific probe that is specific for one of the polymorphism variants is often used in conjunction with the allele-specific probe for the other polymorphism variant. In some embodiments, the probes are immobilized on a solid support and the target sequence in an individual is analyzed using both probes simultaneously. Examples of nucleic acid arrays are described by WO 95/11995. The same array or a different array can be used for analysis of characterized polymorphisms. WO 95/11995 also describes subarrays that are optimized for detection of variant forms of a pre-characterized polymorphism. Such a subarray can be used in detecting the presence of the mutant TYR gene described herein.

8. Sequence-Specific Primers

Mutations are also commonly detected using sequence-specific amplification or primer extension methods. These reactions typically involve use of primers that are designed to specifically target a polymorphism via a mismatch at the 3' end of a primer. The presence of a mismatch effects the ability of a polymerase to extend a primer when the polymerase lacks error-correcting activity. For example, to detect a YR sequence using a TYR-specific amplification- or extension-based method, a primer complementary to the wild type or mutant TYR gene is designed such that the 3' terminal nucleotide hybridizes at the mutation site. The presence of the YR mutation can be determined by the ability of the primer to initiate extension. If the 3' terminus is mismatched, the extension is impeded. Thus, for example, if a primer matches the YR mutation at the 3' end, the primer matches and will be efficiently extended.

Typically, the primer is used in conjunction with a second primer in an amplification reaction. The second primer hybridizes at a site unrelated to the polymorphic position. Amplification proceeds from the two primers leading to a detectable product signifying the particular allelic form is present. Sequence-specific amplification- or extension-based methods are described in, for example, WO 93/22456; U.S. Pat. Nos. 5,137,806; 5,595,890; 5,639,611; and U.S. Pat. No. 4,851,331.

Using sequence-specific amplification-based genotyping, identification of the mutations requires only detection of the presence or absence of amplified target sequences. Methods for the detection of amplified target sequences are well known in the art. For example, gel electrophoresis and probe hybridization assays described are often used to detect the presence of nucleic acids.

In an alternative probe-less method, the amplified nucleic acid is detected by monitoring the increase in the total amount of double-stranded DNA in the reaction mixture, is described, e.g., in U.S. Pat. No. 5,994,056; and European Patent Publication Nos. 487,218 and 512,334. The detection of double-stranded target DNA relies on the increased fluorescence various DNA-binding dyes, e.g., SYBR® Green, exhibit when bound to double-stranded DNA.

As appreciated by one in the art, sequence-specific amplification methods, can be performed in reaction that employ multiple sequence-specific primers to target particular mutations. Primers for such multiplex applications are generally labeled with distinguishable labels or are selected such that the amplification products produced from the target sequences are distinguishable by size. Thus, for example, the presence of both a wild type and mutant TYR gene in a single sample can be identified using a single amplification by gel analysis of the amplification product.

As in the case of sequence-specific probes, a sequence-specific oligonucleotide primer may be exactly complementary to one of the TYR mutants in the hybridizing region or may have some mismatches at positions other than the 3' terminus of the oligonucleotide, which mismatches occur away from the site of the TYR mutation.

D. 5'-nuclease Assay

Genotyping can also be performed using a "TaqMan®" or "5'-nuclease assay", as described in U.S. Pat. Nos. 5,210,015; 5,487,972; and 5,804,375; and Holland et al., 1988, *Proc. Natl. Acad. Sci. USA* 88:7276–7280. In the TaqMan® assay, labeled detection probes that hybridize within the amplified region are added during the amplification reaction. The probes are modified so as to prevent the probes from acting as primers for DNA synthesis. The amplification is performed using a DNA polymerase haveing 5' to 3' exonuclease activity. During each synthesis step of the amplification, any probe which hybridizes to the target nucleic acid downstream from the primer being extended is degraded by the 5' to 3' exonuclease activity of the DNA polymerase. Thus, the synthesis of a new target strand also results in the degradation of a probe, and the accumulation of degradation product provides a measure of the synthesis of target sequences.

The hybridization probe can be a sequence-specific probe that discriminates between wild type and mutant TYR. Alternatively, the method can be performed using a sequence-specific primer and a labeled probe that binds to amplified product.

Any method suitable for detecting degradation product can be used in a 5' nuclease assay. Often, the detection probe is labeled with two fluorescent dyes, one of which is capable of quenching the fluorescence of the other dye. The dyes are attached to the probe, preferably one attached to the 5' terminus and the other is attached to an internal site, such that quenching occurs when the probe is in an unhybridized state and such that cleavage of the probe by the 5' to 3' exonuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673 describe alternative methods for detecting the degradation of probe which occurs concomitant with amplification.

In some cases, mRNA can also be used to determine the whether a cat carries a TYR mutation associated with albinism. Such an analysis can be performed by first reverse-transcribing the target RNA from a biological sample from the cat using, for example, a viral reverse transcriptase, and then amplifying the resulting cDNA; or using a combined high-temperature reverse-transcription-polymerase chain reaction (RT-PCR), as described in U.S. Pat. Nos. 5,310,652; 5,322,770; 5,561,058; 5,641,864; and 5,693,517.

V. Immunological Detection of Mutant TYR

In addition to the identification of albinism carriers by detection of mutant TYR genes and gene expression using nucleic acid hybridization technology, one can also use immunoassays to identify carriers of albinism by detecting mutant TYR or antibodies that specifically bind to them. Immunoassays can be used to qualitatively or quantitatively analyze mutant TYR. A general overview of the applicable technology can be found in Harlow & Lane, Antibodies: A Laboratory Manual (1988).

A. Antibodies to Mutant TYR

Methods of producing polyclonal and monoclonal antibodies that react specifically with mutant TYR, or immunogenic fragments of mutant TYR, are known to those of skill in the art (see, e.g., Coligan, Current Protocols in Immunology (1991); Harlow & Lane, supra; Goding, Monoclonal Antibodies: Principles and Practice (2d ed. 1986); and Kohler & Milstein, Nature 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of immunogens comprising portions of mutant TYR may be used to produce antibodies specifically reactive with mutant TYR or homologues thereof. For example, recombinant mutant TYR (encoded by SEQ ID NOS: 1, 2, or 3) or antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-TYR proteins, using a competitive binding immunoassay. Specific polyclonal antisera and monoclonal antibodies will usually bind with a Kd of at least about 0.1 mM, more usually at least about 1 µM, preferably at least about 0.1 µM or better, and most preferably, 0.01 µM or better. Antibodies specific only for a particular TYR homologue, such as feline TYR, can also be made, by subtracting out other cross-reacting homologues from a species such as a non-human mammal.

Once the specific antibodies against a TYR are available, YR homologues can be detected by a variety of immunoassay methods. For a review of immunological and immunoassay procedures, see Basic and Clinical Immunology (Stites & Terr eds., 7th ed. 1991). Moreover, the immunoassays of the present invention can be performed in any of several configurations, which are reviewed extensively in Enzyme Immunoassay (Maggio, ed., 1980); and Harlow & Lane, supra. Additional assay configurations (i.e., using multiplex assays using microspheres) are described in, e.g., De Jager et al., *Clin. Diagn. Lab. Immunol.* 10(1):13309 (2003); Earley et al., *Cytometry* 50(5):239–42 (2002); and Seidman and Peritt, *J. Immunol. Methods* 267(2):165–71 (2002).

In one exemplary embodiment, the immunoassays are performed using Luminex technology. With Luminex technology, molecular reactions take place on the surface of microscopic beads called microspheres (Literature from Luminex Corporation, Austin, Tex.). For each reaction in a Luminex profile, thousands of molecules are attached to the surface of internally color-coded microspheres. The assigned color-code identifies each reaction throughout the test. The magnitude of the biomolecular reaction is measured using a second molecule called a reporter which can be a secondary antibody labeled with color. The reporter molecule signals the extent of the reaction by attaching to the molecules on the microspheres. Because the reporter's signal is also a color, there are two sources of color, the color-code inside the microsphere and the reporter color on the surface of the microsphere. To perform a test, the color-coded microspheres, reporter molecules, and sample are combined. This mixture is then injected into an instrument that uses microfluidics to align the microspheres in single file where lasers illuminate the colors inside and on the surface of each microsphere. Next, advanced optics capture the color signals. Finally, digital signal processing translates the signals into real-time, quantitative data for each reaction. The advantages of this Luminex techniques are that multiplex antigens representing different pathogens can be tested with single serum sample, therefore, it saves on labor, reagents, time and samples: and that it makes high throughput (20,000 microsphere per second) possible and shortens analysis time. For example, one color coded beads can be coated with wild type TYR, and a different color coded beads can be coated with mutant TYR: and 2 sets of beads can be mixed and reacted with the same fluid sample to determine whether the sample has wild type TYR, mutant TYR, or both by a single test.

B. Immunological Binding Assays

The TYR polypeptides of the invention and antibodies that specifically bind to them can be detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology: Antibodies in Cell Biology, volume 37 (Asai, ed. 1993); Basic and Clinical Immunology (Stites & Terr, eds., 7th ed. 1991). Immunological binding assays (or immunoassays) typically use an antibody that specifically binds to a protein or antigen of choice (in this case TYR or an immunogenic fragment thereof). The antibody (e.g., anti-TYR) may be produced by any of a number of means well known to those of skill in the art and as described above. Alternatively, a protein or antigen of choice (in this case TYR, or an immunogenic fragment thereof ) may be used to bind antibodies that specifically bind to the protein or antigen. The protein or antigen may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled TYR polypeptide or a labeled anti-TYR antibody. Alternatively, the labeling agent may be a third moiety, such a secondary antibody, which specifically binds to the antibody/TYR complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. The streptavidin may be bound to a label or detectable group as discussed below. A variety of detectable moieties are well known to those skilled in the art.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADSTM), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination with antibodies that recognize TYR, or secondary antibodies that recognize anti-TYR antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally, simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

1. Non-Competitive Assay Formats

Immunoassays for detecting TYR or immunogenic fragments thereof in samples may be either competitive or noncompetitive. Noncompetitive immunoassays are assays in which the amount of antigen is directly measured. In one preferred "sandwich" assay, for example, the anti-TYR antibodies can be bound directly to a solid substrate on which they are immobilized. These immobilized antibodies then capture TYR present in the test sample. TYR are thus immobilized and then bound by a labeling agent, such as a second TYR antibody bearing a label. Alternatively, the second antibody may lack a label, but it may, in turn, be bound by a labeled third antibody specific to antibodies of the species from which the second antibody is derived. The second or third antibody is typically modified with a detectable label, such as biotin, to which another molecule specifically binds, e.g., streptavidin, to provide a detectable moiety.

Noncompetitive immunoassays may also be assays in which the amount of anti-TYR antibody is directly measured. TYR or an immunogenic fragment thereof can be bound directly to a solid substrate on which they are immobilized. The immobilized TYR then captures anti-TYR antibodies present in the test sample. Anti-TYR antibodies are thus immobilized and then bound by a labeling agent, such as an anti-Fc antibody bearing a label. The anti-Fc antibody may be, for example, an anti-mouse Fc antibody, an anti-rat Fc antibody, or an anti-rabbit Fc antibody. Those of skill in the art will appreciate that any suitable anti-Fc antibody may be selected for use in this type of assay. Alternatively, the anti-Fc antibody may lack a label, but it may, in turn, be bound by a labeled third antibody specific to antibodies of the species from which the second antibody is derived. The second or third antibody is typically modified with a detectable label, such as biotin, to which another molecule specifically binds, e.g., streptavidin, to provide a detectable moiety.

2. Competitive Assay Formats

In competitive assays, the amount of the TYR present in the sample is measured indirectly by measuring the amount of known, added (exogenous) TYR displaced (competed away) from an anti-TYR antibody by the unknown TYR present in a sample. In one competitive assay, a known amount of the TYR is added to a sample and the sample is then contacted with an antibody that specifically binds to the TYR. The amount of exogenous TYR bound to the antibody is inversely proportional to the concentration of the TYR present in the sample. In a particularly preferred embodiment, the antibody is immobilized on a solid substrate. The amount of TYR bound to the antibody may be determined either by measuring the amount of TYR present in a TYR/antibody complex, or alternatively by measuring the amount of remaining uncomplexed protein. The amount of TYR may be detected by providing a labeled TYR molecule.

A hapten inhibition assay is another preferred competitive assay. In this assay the known TYR is immobilized on a solid substrate. A known amount of anti-TYR antibody is added to the sample, and the sample is then contacted with the immobilized TYR. The amount of anti-TYR antibody bound to the known immobilized TYR is inversely proportional to the amount of TYR present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

3. Cross-Reactivity Determinations

Immunoassays in the competitive binding format can also be used for crossreactivity determinations for TYR homologues. For example, a TYR protein at least partially corresponding to a polypeptide sequence encoded by SEQ ID NOS: 1, 2, or 3 or an immunogenic fragment thereof, (e.g., the polypeptide encoded by exon 29 of TYR, can be immobilized to a solid support. Other proteins such as TYR homologues or other proteins from other cat species, are added to the assay so as to compete for binding of the antisera to the immobilized antigen. The ability of the added proteins to compete for binding of the antisera to the immobilized protein is compared to the ability of the TYR or immunogenic portion thereof to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologues. Antibodies that specifically bind only to TYR, or only to particular homologues of TYR can also be made using this methodology.

The immunoabsorbed and pooled antisera are then used in a competitive binding immunoassay as described above to compare a second protein, thought to be perhaps a TYR homologue or an allele, or polymorphic variant of TYR, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by TYR that is required to inhibit 50% of binding, then the second protein is said to specifically bind to the polyclonal antibodies generated to the respective TYR immunogen.

4. Other Assay Formats

Western blot (immunoblot) analysis is used to detect and quantify the presence of the TYR polypeptides in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind TYR polypeptides. The anti-TYR antibodies specifically bind to TYR on the solid support, thereby forming an antibody-polypeptide complex. These antibodies may be directly labeled or alternatively may be subsequently detected using labeled antibodies (e.g., labeled sheep anti-mouse antibodies) that specifically bind to the anti-TYR antibodies.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.* 5:34–41 (1986)).

5. Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

VI. Tyrosinase Assays

Functional tyrosinase assays known in the art can also be used to identify tyrosinase mutants (see, e.g., Muller et al., *EMBO J.* 7(9):2723–30 (1988); King and Olds, *Am. J. Med. Genet.* 20(1):49–55 (1985). For example, a biological sample from a cat can be contacted with a tyrosinase substrate to determine whether the cat is carrier for a tyrosinase mutation or has a wild-type tyrosinase.

VII. Kits

TYR and its homologues are useful tools for more specific and sensitive identification of albinism carriers in, e.g., cats. TYR specific reagents that specifically hybridize to TYR nucleic acid, such as TYR probes and primers (e.g., as set forth in SEQ ID NOS:4–13), TYR nucleic acids (e.g. as set forth in SEQ ID NOS:1, 2, and 3), and TYR specific reagents that specifically bind to the TYR protein, e.g., TYR antibodies are used to identify albinism carriers.

Nucleic acid assays for the presence of TYR DNA and RNA in a sample include numerous techniques are known to those skilled in the art, such as Southern analysis, northern analysis, dot blots, RNase protection, SI analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., Biotechniques 4:230–250 (1986); Haase et al., Methods in Virology, vol. VII, pp. 189–226 (1984); and Nucleic Acid Hybridization: A Practical Approach (Hames et al., eds. 1987). In addition, TYR protein can be detected with the various immunoassay techniques described above, e.g., ELISA, western blots, etc. The test sample is typically compared to both a positive control (e.g., a sample expressing recombinant TYR) and a negative control. A wide variety of kits and components can be prepared according to the present invention, depending upon the intended user of the kit and the particular needs of the user. For example, the kit can be tailored for in vitro or in vivo assays.

The invention also provides kits and solutions for carrying out the amplification methods of the invention. For example, the invention provides kits that include one or more reaction vessels that have aliquots of some or all of the reaction components of the invention in them. Aliquots can be in liquid or dried form. Reaction vessels can include sample processing cartridges or other vessels that allow for the containment, processing and/or amplification of samples in the same vessel. Such kits allow for ready detection of amplification products of the invention into standard or portable amplification devices. The kits can also include written instructions for the use of the kit to amplify and control for amplification of a target sample.

Kits can include, for instance, amplification reagents comprising primers sufficient to amplify at least two different target sequences, a polynucleotide sequence comprising the sequences of the primers or subsequences of the primers s described herein; and at least one probe for amplifying and detecting the polynucleotide sequence. In addition, the kit can include nucleotides (e.g., A, C, G and T), a DNA polymerase and appropriate buffers, salts and other reagents to facilitate amplification reactions.

In some embodiments, the kits comprise vessels such as sample processing cartridges useful for rapid amplification of a sample as described in Belgrader, et al., *Biosensors and Bioelectronics* 14:849–852 (2000); Belgrader, et al., *Science,* 284:449–450 (1999); and Northrup, M. A., et al. "A New Generation of PCR Instruments and Nucleic Acid Concentration Systems" in PCR PROTOCOLS (Sninsky, J. J. et al (eds.)) Academic, San Diego, Chapter 8 (1998)).

EXAMPLES

The following examples are offered to illustrate, but not to limit the claimed invention.

Example 1

Materials and Methods

Sample Collection and DNA Preparation: Samples from domestic cat breeds were collected by various methods including buccal swabs, EDTA anti-coagulated whole blood via venipuncture, and tissues collected post-euthanasia. Buccal swab samples were collected at various cat breeding shows within the United States and Europe or were requested specifically from particular cats then collected and sent by the breeders. DNA was isolated from buccal swabs following published procedures (Young et al., 2003). DNA was extracted from white cell preparations from whole blood and/or tissues by standard phenol/chloroform extractions.

Primer Design, PCR and Sequencing: Publicly available sequences (GenBank) from various specks were aligned for the gene TYR, including *Homo sapiens*: NM_000372.2, *Oryctolagus cuniculus*: AF210660.1, *Canis familiaris*: AY336053, *Mus musculus*: NM_011661, and *Bos taurus*: AY046527 Primers were developed from conserved regions for each exon using the software Primer3 (Rozen et al., 2000) (Table 1) and tested for efficacy in the cat using PCR conditions as previously described (Lyons et al., 1997) on a Stratagene 96-well temperature gradient Robocycler (Stratagene, La Jolla, Calif.). Primers (Invitrogen Inc., Carlsbad, Calif.) were used to amplify control cat DNA that did not phenotypically show any form of albinism and was not suspected to be a carrier of any albinism mutations. The amplified products were separated on 1.8% agarose gels at 100 V/hr. Gels were visualized by UV exposure after ethidium bromide staining and photo-documented using the Alpha Imaging System (Alpha Innotech Corp, San Leandro, Calif.). A positive optimization of the primers produced a single PCR product that was excised from the gel and purified using the Qiagen gel extraction column (Qiagen Inc., Valencia Calif.), or PCR products were directly purified using the Qiagen PCR clean up kit (Qiagen Inc., Valencia Calif.). Purified products were directly sequenced in both directions using the ABI Dye Terminator Sequencing chemistry v3.1 (Applied Biosystems, Foster City, Calif.). Sequencing reactions were separated on an ABI 377 DNA Analyzer and the DNA contig sequence was assembled using the Sequencer Software package (Gene Codes Corp, Ann Arbor, Mich.). Integrity of the sequence contig was confirmed by visual inspection and verified to be the correct gene by comparison to sequences in GenBank using BLAST (Altschul et al., 1990).

Amplification: TYR exon products were amplified by PCR from genomic DNA of various cats with appropriate phenotypic variations using the optimized primers (Table 1). Individual exons were amplified independently in feline DNA sample using standard PCR conditions on a Stratagene 96-well temperature gradient Robocycler. Approximately 2 μl of buccal swab extracted DNA (estimated to be at least 10 ng) was used per PCR reaction. Reaction conditions for each primer pair were as follows: approximately 1 pmol of each forward and reverse primer, 1.25 mM dNTP, 2.0 mM $MgCl_2$, 1×PCR buffer II and 0.375U of AmpliTaq™ (Applied Biosystems) polymerase in 10 μl reaction volumes. Cycling parameters included an initial 3 min denaturation at 94° C. followed by 35 cycles of: 1 min denaturation at 94° C., annealing for 1 min at 58° C. and a 72° C. extension for 1 min. The cycling parameters were followed by a final extension at 72° C. for 10 min. Random bred and fancy breed cat DNA samples were analyzed from the United States, Eurasia, and Australia. Samples included several "foundation" cat breeds and the breeds that are known to be fixed or segregate for the albinism phenotype, including, Bengal (snow only), Birman, Bombay (sable only), Burmese, Colorpoint Shorthair, Himylayan, Korat, Persian, Ragdoll, random breds, Siamese, Singapura, Sphynx, Tonkinese. At least three samples were analyzed for each population, except only one suspected pointed Sphynx was available. The Colorpoint Shorthair cats (N=33) were the cats from the pedigree that are segregating for albinism. Products were generated, visualized, gel extracted, purified, and sequenced as described above and analyzed for mutations associated with the specific phenotypes. Sequences generated from each exon were aligned (DNAStar, Madison, Wis.) with wild-type sequence from both cat and dog to identify possible causative mutations for the observed phenotype. When polymorphisms were detected, sequence data was translated to determine if the mutation resulted in an amino acid change.

Pedigree Analysis: Samples were collected from cats that formed a multi-generational pedigree that were segregating for the albinism phenotypes. Phenotypes were verified by visual inspection, breeder reports, segregation in pedigrees, and photographs. Relationship of the cats was verified by parentage testing with 10–15 microsatellites following published procedures (Menotti-Raymond et al., 1999). Pigmented cats that produced an albino offspring were assumed to be obligate carriers of the complete albinism allele. Complete litter information was collected from the five mating types that were available in the pedigree (albino×albino; albino×carrier; carrier×carrier; carrier×non-carrier and carrier×unknown).

Example 2

Identification of Albinism Linked Mutations in the Cat TYR Gene

Each TYR exon primer and the product are presented in Table 1. Primers designed for exon 5 failed to generate product in the domestic cat, therefore no further analyses were attempted. The species used for comparison include; *Homo sapiens*: M27 160, *Canis familiaris*: AY336053, *Oryctolagus cuniculus*: AF210660.1, *Mus musculus*: NM_011661, and *Bos taurus*: AY046527. A total of 1100 bp of TYR (46%) was analyzed in the cat (Table 1). The sequence alignment is presented in FIG. 1. The overall homology of the feline TYR sequence to human, dog, rabbit, mouse and cow ranged between 83.7% and 93.8%, the dog having the highest homology and mouse having the lowest homology. Exon 2 had the lowest conservation across all species, the strongest conservation was found in exon 3, where the cat was identical to humans. The protein identity ranged from 88.5% to 94.7% with greatest homology to *Canis familiaris*. The 1100 bp of TYR was analyzed in 70 cats from random bred cats and 13 different breeds. The Burmese allele is a G to T transversion at position 715 of exon 1 resulting in a glycine to tryptophan (amino acid 227) amino acid change. For the Siamese allele, a G to A transition in exon 2 at position 940 (canine reference sequence AY336053) was identified that causes an amino acid change from glycine to arginine (amino acid 302). The albino allele is a C deletion at position 975 causing a frame shift and a premature ochre stop codon 11 amino acids downstream from the mutation. Identical mutations were found in all breeds that had identical phenotypes. Other single nucleotide polymorphisms were identified in TYR, including, a silent mutation in exon 1 found in the Himalayan breed.

Pedigree analysis suggested that complete albinism has an autosomal recessive mode of inheritance. One multi-generational extended pedigree that segregates for the albinism phenotypes was analyzed. All mutations are segregating concordantly with the phenotypes. Cats were identified as carriers if they produced at least one albino kitten. The one albino to albino mating produced only albino cats (Brown et al., Birth Defects Orig Artic Ser, 07, 102–9 (1971)). The single albino to carrier mating resulted in two albinos out of three kittens. The carrier to carrier matings produced 25% albinos, 8 of 32 kittens. Two breedings of a suspected carrier to a cat with unknown carrier status did not produce any albino kittens from 10 offspring. The two unknown carrier status cats were shown by sequence analysis to not carry the albino (c) allele. All non-albino cats had the "pointed" phenotype and were genetically $c^s c^s$ or $c^s c$. These data strongly supported that albinism was an allele to "points" and part of the C locus allelic series. Sequence analysis confirmed that the suspected carriers had one complete albinism allele.

Our analysis of an extended pedigree segregating for albinism confirms that the phenotype is allelic to the mutations in TYR and suggests the allelic series, $C>c^b>c^s>c^a$. The albino cats evaluated in this study have blue eyes. As with most blue-eyed cats, reduced pigment in the tapetum produces "reddish" as opposed to "greenish" tapetal reflection or "eye-shine". The allele "c" has been reserved for red-eyed albino, or for complete albinism. But, the difference in the tapetal reflex suggests that the single report of a red-eyed albino cat may be in error and true albino cats have not yet been documented.

The mutations identified for the three alleles in the cat cause marked amino acid changes that are similar to those found in other species. The burmese allele G to T transversion is found early in the coding sequence in exon 1, resulting in a glycine to tryptophan amino acid change. This change causes a substitution of a small, neutral charge polar with a large hydrophobic non-polar residue. In rabbits, the burmese coloration is termed "chinchilla" and two nucleotide variants have been identified in animals with this phenotype (Aigner et al., 2000). These variants cause amino acid changes from glutamic acid to glycine and threonine to an isoleucine, and are also found in exon 1. The cat mutation is found at nucleotide 715 and the rabbit mutations are slightly more downstream at nucleotides 881 and 1073. This data suggests that minor amino acid changes early in the coding sequence will affect coloration, but with a milder phenotypic affect.

For the Siamese allele, the G to A transition in exon 2 at position 940 (canine reference sequence AY336053) causes an amino acid change from glycine to arginine, another large amino acid. The same phenotype in mice and rabbits result from mutations in exon 1 (Aigner et al., 2000; Petrij et al., 2001).

The albino allele is a C deletion in exon 2 at position 975 (canine reference sequence AY336053) causing a frame shift and a premature ochre stop codon 11 amino acids downstream from the mutation. Identical mutations were found in all breeds that had identical phenotypes.

If adopted at genetic tests for color, the mutations described herein can improve the efficiency of breeding programs for a variety of breeds.

It is understood that the examples and embodiments described herein are for illustrative purposes only and that various modifications or changes in light thereof will be suggested to persons skilled in the art and are to be included within the spirit and purview of this application and scope of the appended claims. All publications, accession numbers, patents, and patent applications cited herein are hereby incorporated by reference in their entirety for all purposes.

---

What is claimed is:

1. A method for detecting a mutation associated with a Siamese phenotype in a domesticated cat, said method comprising: obtaining a biological sample from the domesticated cat and detecting a nucleic acid sequence comprising position 40 of SEQ ID NO:2, wherein detection of an A at position 40 of SEQ ID NO: 2 is indicative of a mutation associated with the Siamese phenotype in the domestic cat.

2. The method of claim 1, wherein the nucleic acid sequence is detected by:
   (a) specifically amplifying a subsequence of a gene encoding TYR, wherein the subsequence comprises position 40 of SEQ ID NO:2 in the biological sample, thereby amplifying nucleic acids comprising the mutation; and
   (b) detecting the amplified nucleic acids, thereby detecting the mutation.

3. The method of claim 2, wherein the subsequence is specifically amplified using primers comprising the sequences set forth in SEQ ID NOS: 6, and 7.

4. The method of claim 2, wherein the amplified nucleic acids are detected by sequencing.

5. The method of claim 2, wherein the mutation is detected by contacting the amplified nucleic acids with a restriction enzyme.

6. The method of claim 5, wherein the restriction enzyme is Hpa II.

7. The method of claim 1, wherein the mutation is detected by single base extension.

8. The method of claim 2, wherein the amplified nucleic acids are detected by sequence specific hybridization using an allele specific oligonucleotide.

9. The method of claim 8, wherein the sequence specific hybridization is performed as a dot blot.

10. The method of claim 8, wherein the sequence specific hybridization is performed as a reverse dot blot.

11. The method of claim 1, wherein the mutation is detected by 5' nuclease assay or TaqMan® assay.

* * * * *

SEQUENCE LISTING

<160> NUMBER OF SEQ ID NOS: 39

<210> SEQ ID NO 1
<211> LENGTH: 678
<212> TYPE: DNA
<213> ORGANISM: Felis catus
<220> FEATURE:
<223> OTHER INFORMATION: tyrosinase (TYR) exon 1 variant, Burmese
      phenotype

<400> SEQUENCE: 1

```
agcctgatgg agaaggaatg ctgtccagcg tggacgggtg acagcagtcc ctgcggccag      60
ctctcaggca ggggtgcctg tcaggacatc acgctgtcca aagctccact cgggcctcaa     120
taccccttca cggggatgga tgaccgggag gcctggccct ccgtcttta taatcggacc     180 tgccagtgct ttggcaactt catgggattc aactgtggaa attgcaagtt tggcttttgg     240
ggaccaaact gcacagagaa gcgacttttg gtgagaagaa acatctttga tttgagcgtc     300
ccagagaaga acaaatttct tgcctacctc actttagcga agcatactat cagcccagac     360
tatgtcatcc ccataggcac ctatggccaa atgaataatg gatctacacc catgtttaat     420
gacatcaatg tttatgacct cttcgtctgg atgcattact atgtgtcaag ggacacactg     480
cttggagggt ctgaaatctg gaaagacatt gattttgctc atgaagcccc tggtttcctg     540
ccttggcaca gactcttctt gttgctgtgg gaacaagaaa tccagaagct gacctgggat     600
gagaacttca ctattccata ttgggattgg cgagatgcta aaagctgtga catttgcaca     660
```

```
gatgagtaca tgggaggg                                                    678

<210> SEQ ID NO 2
<211> LENGTH: 144
<212> TYPE: DNA
<213> ORGANISM: Felis catus
<220> FEATURE:
<223> OTHER INFORMATION: tyrosinase (TYR) exon 2 variant, Siamese
      phenotype

<400> SEQUENCE: 2
tgtgatggaa ctccagaggg accattactg cgcaatccca gaaaccatga caaagccagg     60
accccaaggc tccctcctc tgctgatgtg gaattttgcc taagtctgac acaatatgaa     120
tcgggttcca tggataaagc tgca                                           144

<210> SEQ ID NO 3
<211> LENGTH: 143
<212> TYPE: DNA
<213> ORGANISM: Felis catus
<220> FEATURE:
<223> OTHER INFORMATION: tyrosinase (TYR) exon 2 variant, albino
      phenotype

<400> SEQUENCE: 3
tgtgatggaa ctccagaggg accattactg cgcaatcccg gaaaccatga caaagccagg     60
accccaaggc tccctcctct gctgatgtgg aattttgcct aagtctgaca caatatgaat    120
cgggttccat ggataaagct gca                                            143

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:tyrosinase
      (TYR) exon 1 conserved region PCR amplification 5'
      forward primer

<400> SEQUENCE: 4
ctgcctgctg tggagtttc                                                  19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:tyrosinase
      (TYR) exon 1 conserved region PCR amplification 3'
      reverse primer

<400> SEQUENCE: 5
agaatgatgc tgggctgagt                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:tyrosinase
      (TYR) exon 2 conserved region PCR amplification 5'
      forward primer

<400> SEQUENCE: 6
tagccgattg gaggatacaa                                                 20
```

```
<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:tyrosinase
      (TYR) exon 2 conserved region PCR amplification 3'
      reverse primer

<400> SEQUENCE: 7
gcagctttat ccatggaacc                                                   20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:tyrosinase
      (TYR) exon 3 conserved region PCR amplification 5'
      forward primer

<400> SEQUENCE: 8
cttactggga tagcggatgc                                                   20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:tyrosinase
      (TYR) exon 3 conserved region PCR amplification 3'
      reverse primer

<400> SEQUENCE: 9
caaatgcatg gtgaagaagg                                                   20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:tyrosinase
      (TYR) exon 4 conserved region PCR amplification 5'
      forward primer

<400> SEQUENCE: 10
tatttttgag cagtggctcc                                                   20

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:tyrosinase
      (TYR) exon 4 conserved region PCR amplification 3'
      reverse primer

<400> SEQUENCE: 11
ttgtagatag ctatagtcat agcccag                                           27

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:tyrosinase
      (TYR) exon 5 conserved region PCR amplification 5'
      forward primer
```

```
<400> SEQUENCE: 12
tcagacccag actcttttca ag                                              22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:tyrosinase
      (TYR) exon 5 conserved region PCR amplification 3'
      reverse primer

<400> SEQUENCE: 13
ctttctccat gaggagtggc                                                 20

<210> SEQ ID NO 14
<211> LENGTH: 60
<212> TYPE: DNA
<213> ORGANISM: Felis catus and Canis familiaris
<220> FEATURE:
<223> OTHER INFORMATION: domestic cat (Fcat) wildtype (wt) and Persian
      (Pe), dog (Cfam) and consensus (Majority)
      tyrosinase (TYR) exon 1

<400> SEQUENCE: 14
ccttggcaca gactcttctt gttgctgtgg gaacaagaaa tccagaagct gaccggggat     60

<210> SEQ ID NO 15
<211> LENGTH: 60
<212> TYPE: DNA
<213> ORGANISM: Mus musculus
<220> FEATURE:
<223> OTHER INFORMATION: mouse (Mmus) tyrosinase (TYR) exon 1

<400> SEQUENCE: 15
ccttggcaca gacttttctt gttattgtgg gaacaagaaa ttcgagaact aactggggat     60

<210> SEQ ID NO 16
<211> LENGTH: 60
<212> TYPE: DNA
<213> ORGANISM: Oryctolagus cuniculus
<220> FEATURE:
<223> OTHER INFORMATION: rabbit (Ocun) tyrosinase (TYR) exon 1

<400> SEQUENCE: 16
ccttggcaca gactcttctt gttgctgtgg gaacaagaaa tccagaagct gacaggggat     60

<210> SEQ ID NO 17
<211> LENGTH: 60
<212> TYPE: DNA
<213> ORGANISM: Felis catus
<220> FEATURE:
<223> OTHER INFORMATION: domestic cat (Fcat) Burmese (Bu) tyrosinase
      (TYR) exon 1 Burmese mutation

<400> SEQUENCE: 17
ccttggcaca gactcttctt gttgctgtgg gaacaagaaa tccagaagct gacctgggat     60

<210> SEQ ID NO 18
<211> LENGTH: 60
<212> TYPE: PRT
<213> ORGANISM: Felis catus and Canis familiaris
<220> FEATURE:
<223> OTHER INFORMATION: domestic cat (Fcat) wildtype (wt) and Persian
      (Pe), dog (Cfam) and consensus (Majority)
      tyrosinase (TYR) exon 1 translation
```

-continued

```
<400> SEQUENCE: 18

Leu Gly Gly Ser Glu Ile Trp Lys Asp Ile Asp Phe Ala His Glu Ala
 1               5                  10                  15

Pro Gly Phe Leu Pro Trp His Arg Leu Phe Leu Leu Trp Glu Gln
            20                  25                  30

Glu Ile Gln Lys Leu Thr Gly Asp Glu Asn Phe Thr Ile Pro Tyr Trp
        35                  40                  45

Asp Trp Arg Asp Ala Lys Ser Cys Asp Ile Cys Thr
50                  55                  60

<210> SEQ ID NO 19
<211> LENGTH: 60
<212> TYPE: PRT
<213> ORGANISM: Mus musculus
<220> FEATURE:
<223> OTHER INFORMATION: mouse (Mmus) tyrosinase (TYR) exon 1
      translation

<400> SEQUENCE: 19

Leu Gly Gly Ser Glu Ile Trp Arg Asp Ile Asp Phe Ala His Glu Ala
 1               5                  10                  15

Pro Gly Phe Leu Pro Trp His Arg Leu Phe Leu Leu Trp Glu Gln
            20                  25                  30

Glu Ile Arg Glu Leu Thr Gly Asp Glu Asn Phe Thr Val Pro Tyr Trp
        35                  40                  45

Asp Trp Arg Asp Ala Glu Asn Cys Asp Ile Cys Thr
50                  55                  60

<210> SEQ ID NO 20
<211> LENGTH: 60
<212> TYPE: PRT
<213> ORGANISM: Oryctolagus cuniculus
<220> FEATURE:
<223> OTHER INFORMATION: rabbit (Ocun) tyrosinase (TYR) exon 1
      translation

<400> SEQUENCE: 20

Leu Gly Gly Ser Glu Val Trp Arg Asp Ile Asp Phe Ala His Glu Ala
 1               5                  10                  15

Pro Gly Phe Leu Pro Trp His Arg Leu Phe Leu Leu Trp Glu Gln
            20                  25                  30

Glu Ile Gln Lys Leu Thr Gly Asp Glu Asn Phe Thr Ile Pro Tyr Trp
        35                  40                  45

Asp Trp Arg Asp Ala Glu Ser Cys Asp Val Cys Thr
50                  55                  60

<210> SEQ ID NO 21
<211> LENGTH: 60
<212> TYPE: PRT
<213> ORGANISM: Felis catus
<220> FEATURE:
<223> OTHER INFORMATION: domestic cat (Fcat) Burmese (Bu) tyrosinase
      (TYR) exon 1 Burmese mutation translation

<400> SEQUENCE: 21

Leu Gly Gly Ser Glu Ile Trp Lys Asp Ile Asp Phe Ala His Glu Ala
 1               5                  10                  15

Pro Gly Phe Leu Pro Trp His Arg Leu Phe Leu Leu Trp Glu Gln
            20                  25                  30

Glu Ile Gln Lys Leu Thr Trp Asp Glu Asn Phe Thr Ile Pro Tyr Trp
        35                  40                  45
```

Asp Trp Arg Asp Ala Lys Ser Cys Asp Ile Cys Thr
        50                  55                  60

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence:consensus
      (Majority) tyrosinase (TYR) exon 2

<400> SEQUENCE: 22
gcgcaatcct ggaaaccatg acaaagccag daccccaagg ctcccctcct ctgctgatgt     60

<210> SEQ ID NO 23
<211> LENGTH: 60
<212> TYPE: DNA
<213> ORGANISM: Mus musculus
<220> FEATURE:
<223> OTHER INFORMATION: mouse (Mmus) tyrosinase (TYR) exon 2

<400> SEQUENCE: 23
acgtaatcct ggaaaccatg acaaagccaa aaccccagg ctcccatctt cagcagatgt     60

<210> SEQ ID NO 24
<211> LENGTH: 60
<212> TYPE: DNA
<213> ORGANISM: Oryctolagus cuniculus
<220> FEATURE:
<223> OTHER INFORMATION: rabbit (Ocun) tyrosinase (TYR) exon 2

<400> SEQUENCE: 24
gcgcaatcct ggaaaccatg acaaagccag gactccgagg ctcccctcct catcagatgt     60

<210> SEQ ID NO 25
<211> LENGTH: 60
<212> TYPE: DNA
<213> ORGANISM: Canis familiaris
<220> FEATURE:
<223> OTHER INFORMATION: dog (Cfam) tyrosinase (TYR) exon 2

<400> SEQUENCE: 25
gcgcaatcct gggaaccatg acaaagccag daccccaaga ctcccctcct ctgctgatgt     60

<210> SEQ ID NO 26
<211> LENGTH: 60
<212> TYPE: DNA
<213> ORGANISM: Felis catus
<220> FEATURE:
<223> OTHER INFORMATION: domestic cat (Fcat) wildtype (wt) and Burmese
      (Bu) tyrosinase (TYR) exon 2

<400> SEQUENCE: 26
gcgcaatccc ggaaaccatg acaaagccag daccccaagg ctcccctcct ctgctgatgt     60

<210> SEQ ID NO 27
<211> LENGTH: 60
<212> TYPE: DNA
<213> ORGANISM: Felis catus
<220> FEATURE:
<223> OTHER INFORMATION: domestic cat (Fcat) Persian (Pe) tyrosinase
      (TYR) exon 2 Siamese mutation

<400> SEQUENCE: 27
gcgcaatccc agaaaccatg acaaagccag daccccaagg ctcccctcct ctgctgatgt     60

<210> SEQ ID NO 28
<211> LENGTH: 59
<212> TYPE: DNA
<213> ORGANISM: Felis catus
<220> FEATURE:
<223> OTHER INFORMATION: domestic cat (Fcat) albino mutation (alb)
      tyrosinase (TYR) exon 2

<400> SEQUENCE: 28
gcgcaatccc ggaaaccatg acaaagccag gaccccaagg ctccctcctc tgctgatgt      59

<210> SEQ ID NO 29
<211> LENGTH: 48
<212> TYPE: PRT
<213> ORGANISM: Felis catus
<220> FEATURE:
<223> OTHER INFORMATION: domestic cat (Fcat) wildtype (wt) and Burmese
      (Bu) and consensus (Majority) tyrosinase (TYR) exon 2 translation

<400> SEQUENCE: 29

Cys Asp Gly Thr Pro Glu Gly Pro Leu Leu Arg Asn Pro Gly Asn His
  1               5                  10                  15

Asp Lys Ala Arg Thr Pro Arg Leu Pro Ser Ser Ala Asp Val Glu Phe
             20                  25                  30

Cys Leu Ser Leu Thr Gln Tyr Glu Ser Gly Ser Met Asp Lys Ala Ala
         35                  40                  45

<210> SEQ ID NO 30
<211> LENGTH: 48
<212> TYPE: PRT
<213> ORGANISM: Mus musculus
<220> FEATURE:
<223> OTHER INFORMATION: mouse (Mmus) tyrosinase (TYR) exon 2
      translation

<400> SEQUENCE: 30

Cys Asp Gly Thr Pro Glu Gly Pro Leu Leu Arg Asn Pro Gly Asn His
  1               5                  10                  15

Asp Lys Ala Lys Thr Pro Arg Leu Pro Ser Ser Ala Asp Val Glu Phe
             20                  25                  30

Cys Leu Ser Leu Thr Gln Tyr Glu Ser Gly Ser Met Asp Arg Thr Ala
         35                  40                  45

<210> SEQ ID NO 31
<211> LENGTH: 48
<212> TYPE: PRT
<213> ORGANISM: Oryctolagus cuniculus
<220> FEATURE:
<223> OTHER INFORMATION: rabbit (Ocun) tyrosinase (TYR) exon 2
      translation

<400> SEQUENCE: 31

Cys Asn Ala Thr Ser Glu Gly Pro Leu Leu Arg Asn Pro Gly Asn His
  1               5                  10                  15

Asp Lys Ala Arg Thr Pro Arg Leu Pro Ser Ser Ser Asp Val Glu Phe
             20                  25                  30

Cys Leu Ser Leu Thr Gln Tyr Glu Ser Gly Ser Met Asp Lys Ala Ala
         35                  40                  45

<210> SEQ ID NO 32
<211> LENGTH: 48
<212> TYPE: PRT
<213> ORGANISM: Canis familiaris
<220> FEATURE:

-continued

<223> OTHER INFORMATION: dog (Cfam) tyrosinase (TYR) exon 2 translation

<400> SEQUENCE: 32

Cys Asp Gly Thr Pro Glu Gly Pro Leu Leu Arg Asn Pro Gly Asn His
 1               5                  10                  15

Asp Lys Ala Arg Thr Pro Arg Leu Pro Ser Ser Ala Asp Val Glu Phe
            20                  25                  30

Cys Leu Ser Leu Thr Gln Tyr Glu Ser Asp Ser Met Asp Lys Ala Ala
        35                  40                  45

<210> SEQ ID NO 33
<211> LENGTH: 48
<212> TYPE: PRT
<213> ORGANISM: Felis catus
<220> FEATURE:
<223> OTHER INFORMATION: domestic cat (Fcat) Persian (Pe) tyrosinase
      (TYR) exon 2 Siamese mutation translation

<400> SEQUENCE: 33

Cys Asp Gly Thr Pro Glu Gly Pro Leu Leu Arg Asn Pro Arg Asn His
 1               5                  10                  15

Asp Lys Ala Arg Thr Pro Arg Leu Pro Ser Ser Ala Asp Val Glu Phe
            20                  25                  30

Cys Leu Ser Leu Thr Gln Tyr Glu Ser Gly Ser Met Asp Lys Ala Ala
        35                  40                  45

<210> SEQ ID NO 34
<211> LENGTH: 48
<212> TYPE: PRT
<213> ORGANISM: Felis catus
<220> FEATURE:
<223> OTHER INFORMATION: domestic cat (Fcat) albino mutation (alb)
      tyrosinase (TYR) exon 2 translation

<400> SEQUENCE: 34

Cys Asp Gly Thr Pro Glu Gly Pro Leu Leu Arg Asn Pro Gly Asn His
 1               5                  10                  15

Asp Lys Ala Arg Thr Pro Arg Leu Pro Pro Leu Leu Met Trp Asn Phe
            20                  25                  30

Ala Leu Val Leu His Asn Met Asn Arg Val Pro Trp Ile Lys Leu His
        35                  40                  45

<210> SEQ ID NO 35
<211> LENGTH: 426
<212> TYPE: DNA
<213> ORGANISM: Felis catus
<220> FEATURE:
<223> OTHER INFORMATION: GenBank Accession No. AY012029 partial feline
      tyrosinase (TYR) coding sequence

<400> SEQUENCE: 35
gcctgtcagg acatcacgct gtccaaagct ccactcgggc tcaataccc cttcacgggg      60 atggatgacc gggaggcctg gccctccgtc ttttataatc ggacctgcca gtgctttggc    120
aacttcatgg gattcaactg tggaaattgc aagtttggct tttggggacc aaactgcaca    180
gagaagcgac ttttggtgag aagaaacatc tttgatttga gcgtcccaga agaacaaa     240 tttcttgcct acctcacttt agcgaagcat actatcagcc agactatgt catccccata    300 ggcacctatg gccaaatgaa taatggatct acacccatgt taatgacat caatgtttat    360 gacctcttcg tctggatgca ttactatgtg tcaagggaca cactgcttgg agggtctgaa    420
atctgg                                                              426

```
<210> SEQ ID NO 36
<211> LENGTH: 244
<212> TYPE: DNA
<213> ORGANISM: Felis catus
<220> FEATURE:
<223> OTHER INFORMATION: GenBank Accession No. U40716 partial feline
      tyrosinase (TYR) coding sequence

<400> SEQUENCE: 36
gattggagga gtacaatagc cgtcaggctt tatgtgatgg aactccagag ggaccattac     60
tgcgcaatcc cggaaaccat gacaaagcca ggacccaag gctcccctcc tctgctgatg    120
tggaattttg cctaagtctg acacaatatg aatcggattc catggataaa gctgccaatt   180
tcagctttag gaatacactg gaaggatttg ctagtccact tactgggata gcagatgcct   240
ctca                                                                 244

<210> SEQ ID NO 37
<211> LENGTH: 142
<212> TYPE: PRT
<213> ORGANISM: Felis catus
<220> FEATURE:
<223> OTHER INFORMATION: GenBank Accession No. AAG38772 partial feline
      tyrosinase (TYR) encoded by GenBank Accession No.
      AY012029

<400> SEQUENCE: 37

Ala Cys Gln Asp Ile Thr Leu Ser Lys Ala Pro Leu Gly Pro Gln Tyr
 1               5                  10                  15

Pro Phe Thr Gly Met Asp Asp Arg Glu Ala Trp Pro Ser Val Phe Tyr
                20                  25                  30

Asn Arg Thr Cys Gln Cys Phe Gly Asn Phe Met Gly Phe Asn Cys Gly
            35                  40                  45

Asn Cys Lys Phe Gly Phe Trp Gly Pro Asn Cys Thr Glu Lys Arg Leu
        50                  55                  60

Leu Val Arg Arg Asn Ile Phe Asp Leu Ser Val Pro Glu Lys Asn Lys
 65                  70                  75                  80

Phe Leu Ala Tyr Leu Thr Leu Ala Lys His Thr Ile Ser Pro Asp Tyr
                85                  90                  95

Val Ile Pro Ile Gly Thr Tyr Gly Gln Met Asn Asn Gly Ser Thr Pro
            100                 105                 110

Met Phe Asn Asp Ile Asn Val Tyr Asp Leu Phe Val Trp Met His Tyr
        115                 120                 125

Tyr Val Ser Arg Asp Thr Leu Leu Gly Gly Ser Glu Ile Trp
    130                 135                 140

<210> SEQ ID NO 38
<211> LENGTH: 80
<212> TYPE: PRT
<213> ORGANISM: Felis catus
<220> FEATURE:
<223> OTHER INFORMATION: GenBank Accession No. AAB08729 partial feline
      tyrosinase (TYR) encoded by GenBank Accession No.
      U40716

<400> SEQUENCE: 38

Leu Glu Glu Tyr Asn Ser Arg Gln Ala Leu Cys Asp Gly Thr Pro Glu
 1               5                  10                  15

Gly Pro Leu Leu Arg Asn Pro Gly Asn His Asp Lys Ala Arg Thr Pro
                20                  25                  30
```

```
Arg Leu Pro Ser Ser Ala Asp Val Glu Phe Cys Leu Ser Leu Thr Gln
         35                  40                  45

Tyr Glu Ser Asp Ser Met Asp Lys Ala Ala Asn Phe Ser Phe Arg Asn
     50                  55                  60

Thr Leu Glu Gly Phe Ala Ser Pro Leu Thr Gly Ile Ala Asp Ala Ser
 65                  70                  75                  80

<210> SEQ ID NO 39
<211> LENGTH: 1657
<212> TYPE: DNA
<213> ORGANISM: Canis familiaris
<220> FEATURE:
<223> OTHER INFORMATION: GenBank Accession No. AY336053 tyrosinase (TYR)
      mRNA complete CDS canine reference sequence

<400> SEQUENCE: 39
tttcctgcag accttgtgag gactagagga agaagaatgc tcctggctgc tttgtgctgt      60
ctgctgtgga gtttccgaac ctccactggc catttccctc gagcctgtgc ctcctccaag     120
agcctgatgg agaaggaatg ctgcccacca tggagtggtg acgggagtcc ctgtggccag     180 cttttcaggca ggggtgcctg tcaggacatc atactatcca atgccccatt cgggcctcag     240
ttccccttca cggggggtgga tgaccgggaa tcttggcctt ctgtctttta caatcggacc     300
tgccagtgct ttggtaactt catgggattc aactgtggaa attgcaagtt ggcttttgg      360 ggacaaaact gcacagagaa gcgacttttg gtgagaaaaa acatctttga tttgagtgtc     420
ccagagaaga caaatttct tgcctacctt actttagcaa agcatactac cagcccagac     480
tatgtcatcc ccacaggtac ctatggccaa atgaataatg gatcaacacc catgtttaat     540
gacatcaaca tttatgatct cttttgtctgg atgcattatt atgtgtcaag ggacacactg     600
cttggagggt ctgaaatctg gaaagacatt gattttgctc atgaagcccc aggtttcctg     660
ccttggcaca gactcttctt gttgctgtgg gaacaagaaa tccagaagct gaccggggat     720
gagaacttca ctattccata tgggattgg cgagatgcta aaagctgtga catttgcaca     780
gatgagtaca tgggagggcg caacccagca aacccaaact actcagcccc agcatccttc     840
ttctcctctt ggcagatcgt ctgcacccga ctggaggagt acaacagccg acaggctta     900 tgcgatggaa ctccagaagg accgttactg cgcaatcctg ggaaccatga caaagccagg     960 acccaagac tcccctcctc tgctgatgtg gaattctgcc tgagtctgac ccagtatgaa     1020
tcggattcca tggataaagc tgccaatttc agctttagaa atacactgga aggatttgct     1080
agtccactta ctgggatagc agatgcctct caaagcagta tgcacaatgc cttgcatatc     1140
tatatgaatg gaacaatgtc tcaggtaccg ggatctgcca atgatcccat ttttcttctt     1200
caccatgcat tcgttgacag tatttttgag cagtggctcc gaaggcacca tcctcttcga     1260
gaagtttatc cagaagccaa tgctcctatt ggacacaacc gggaatccta catggttcct     1320
tttatacctc tgtacagaaa tggtgatctc tttatttcat ccagagatct ggctatgac     1380 tatagcaacc tacaagaatc agaacggac attttttcaag attacattaa gccctactta     1440
gaacaagcaa gtcggatctg gccatggctc attgggctg ctgtggtagg ctgtgtcgtc     1500
actgctgtgc taggagggct caccagccta ttgtgtcggc gcaatagaaa gcagctccat     1560
gaagaaaagc agccactcct catggaaaag gaggattacc acagcttgtt gtatcagacc     1620
catctataaa aggcttaggc aatagagtag ggccaaa                              1657
```